(12) United States Patent
Jeong

(10) Patent No.: US 7,901,938 B2
(45) Date of Patent: Mar. 8, 2011

(54) METHOD FOR MASS PRODUCTION OF SEEDLING OF SEED POTATO

(75) Inventor: Woo-choon Jeong, Chungcheongbuk-do (KR)

(73) Assignee: Koesan County, Chungcheongbuk-Do (KR)

( * ) Notice: Subject to any disclaimer, the term of this patent is extended or adjusted under 35 U.S.C. 154(b) by 0 days.

(21) Appl. No.: 12/622,190

(22) Filed: Nov. 19, 2009

(65) Prior Publication Data
US 2010/0064582 A1    Mar. 18, 2010

Related U.S. Application Data

(62) Division of application No. 11/552,265, filed on Oct. 24, 2006.

(30) Foreign Application Priority Data

Oct. 24, 2005  (KR) ............................... 2005-100458
Oct. 31, 2005  (KR) ............................... 2005-103491

(51) Int. Cl.
*C12N 5/00*    (2006.01)
*C12N 5/02*    (2006.01)
(52) U.S. Cl. .................... 435/429; 435/420; 435/431
(58) Field of Classification Search ............... 435/420, 435/429, 431
See application file for complete search history.

(56) References Cited

U.S. PATENT DOCUMENTS

| 5,498,541 A | 3/1996 | Oka et al. |
| 5,854,066 A | 12/1998 | Oka |
| 5,992,090 A * | 11/1999 | Stutte et al. ............... 47/58.1 R |

OTHER PUBLICATIONS

Lee et al. "Effects of Quantum Flux Density on Photosynthesis and Chloroplast Ultrastructure in Tissue-Cultured Plantlets and Seedlings of *Liquidambar styraciflua* L. towards Improved Acclimatization and Field Survival," Plant Physiol. (1985) 78, pp. 637-641.*
Akita et al., "Stimulation of potato (*Solanum tuberosum* L.) tuberization by semi continuous liquid medium surface level control," Plant Cell reports (1994) 13:184-187.
Jiménez et al., "Improved production of potato microtubers using a temporary immersion system," Plant Cell. Tissue and Organ Culture 69: 19-23, 1999.

* cited by examiner

*Primary Examiner* — Susan B McCormick Ewoldt
(74) *Attorney, Agent, or Firm* — Locke Lord Bissell & Liddell LLP

(57) ABSTRACT

A method of mass producing potato seedlings, involves collecting growing points of seed potatoes and culturing the growing points in a liquid or solid medium; introducing in vitro plantlets obtained from the culture of the growing points to solid culture; and removing the in vitro plantlets from the solid culture, and planting through stem cutting and acclimatizing the in vitro plantlets in deep flow culture, in which a nutrient solution is circulating. Upon planting in hydroponic facilities, such potato seedlings have high adaptability to the external environment and thus rapidly, uniformly generate roots in a short time. The rapid root anchoring prevents planted seedlings from withering, leading to death, growing poorly, and the like. The direct planting of in vitro plantlets through stem cutting without a separate acclimatization process shortens the overall production period of potato seedlings by omitting the acclimatization process.

8 Claims, 21 Drawing Sheets

METHOD FOR MASS PRODUCTION OF SEEDLING OF SEED POTATO

CROSS-REFERENCE TO RELATED APPLICATIONS

This application is a divisional of U.S. patent application Ser. No. 11/552,265 filed Oct. 24, 2006 and based on and claims priority to Korean Patent Application Nos. 2005-100458 and 2005-103491 filed on Oct. 24 and 31, 2005, respectively, as well as being related to an application entitled AN APPARATUS FOR USE WITH A METHOD FOR MASS PRODUCTION OF SEEDLING OF SEED POTATO filed concurrently herewith, all of which are incorporated herein by reference in their entirety.

FIELD OF THE INVENTION

The present invention relates to a method of mass producing potato seedlings, and more particularly to a method of mass producing high-quality disease-free potato seedlings, suitable for hydroponic growth, within a short period of time.

BACKGROUND

In the production of seed potatoes in hydroponics, it is most important to produce disease-free potato seedlings, which are not infected with viruses and do not have seed-transmissible diseases, and to mass produce high quality potato seedlings within a short period of time.

Once potato seedlings planted in culture beds for producing seed potatoes become infected with viruses or develop major plant diseases, seed potatoes obtained from the infected seedlings are also infected with viruses or have major plant diseases through permanent seed transmission, thereby losing their value as seed potatoes.

Thus, potato seedlings, which are used as starting materials in the production of disease-free seed potatoes, should be obtained from virus-free seedlings, which are propagated through in vitro tissue culture.

In addition, tissue-cultured seedlings, which are produced under culture conditions of high humidity and low light levels, mostly wither and die when they are removed and immediately planted in the external air because the seedlings are grown in an in vitro-culture vessel, which has a low flow of gas and energy and a small temperature change but has a relatively high humidity and a large diurnal change of $CO_2$ concentration. The $CO_2$ concentration inside the closed culture vessel is about 100 µmole·m−1, which is lower than 350 µmole/m−2·s−1, during the day, but sharply increases to 3,000-9,000 µmole·m−1 in the dark. A large quantity of ethylene gas is generated in the vessel because the culture medium is supplemented with sugars, salts and growth regulators and the culture vessel is completely closed to exclude external contaminants and thus prevent contamination. Also, since seedlings growing in the vessel have low growth rates due to the high humidity inside the culture vessel and thus have morphology characterized by long internode lengths, thin stems and narrow leaves, they are not suitable for planting in hydroponics using a nutrient solution.

In vitro propagation through tissue culture, that is, solid culture, liquid culture or tank culture, incurs a high cost for seedling production. This is because the mass production of genetically homogenous seedlings generates completely functional individual plants through culture under suitably sterile conditions, and thus is achieved with facilities having expensive equipment and maintained under suitable conditions. Also, since the entire process is done manually and depends on experience, the labour cost accounts for about one half of the production cost. Also, plantlets grow slowly during propagation and are unable to adapt to the external environment during the acclimatization process, resulting in low survival rates.

To be planted in greenhouse or other culture systems with a nutrient solution, plantlets growing in culture bottles need to be stimulated to grow at the maximum rate and to grow into robust seedlings capable of surviving external stresses when exposed to the external environment. Thus, it is important in the production of potato seedlings to improve the survival rates and quality of plantlets by suitably controlling the acclimatization of plantlets using an artificial method.

Potato seedlings may be produced by a method in which in vitro-cultured plantlets are acclimatized to become potato seedlings, which are then planted, or by another method in which minitubers weighing less than 5 g, which are more difficult to provide for direct sowing in field of in vitro-produced artificial seed potatoes or hydroponically grown seed potatotes, are awoken from dormancy, allowed to sprout and grow to about 7-8 cm in a sterile medium (perlite), and immediately planted as seedlings for planting in hydroponics after mother potatoes are removed therefrom.

The acclimatization of in vitro-cultured plantlets to obtain potato seedlings can be achieved using a method of producing seed potatoes, through on cutting and planting in vitro-culture acclimatized plantlets in sterile perlite culture to form new roots, or using a method of producing seed potatoes by acclimatizing in vitro-cultured plantlets in deep flow hydroponics to which a nutrient solution is supplied through a predetermined procedure and planting the acclimatized plantlets after conducting stem cutting.

The production of potato seedlings through culture in perlite is achievable by allowing plantlets to grow in in vitro culture bottles in a greenhouse having the same environment as a culture room, in which the temperature and light intensity are slowly increased, and air humidity is controlled by widening holes in the entrance. The in vitro-cultured plantlets thus acclimatized are removed from the culture bottles, rinsed with pure water, and planted in a small-scale sterile perlite container for raising seedlings through cut planting or stem cutting to develop new roots on the stems, thereby functioning as seed potatoes. However, there is a very significant problem with this system, as follows. When the planted potato seedlings are exposed to high air humidity or frequent water supply during acclimatization, stems at regions of the plant that contact the perlite in order to develop new roots become very soft and rot. Thus, rooted individuals are poorly acclimatized, and thus show low survival. Also, since very high light levels cause stems to wither, growers should suitably control the light intensity during acclimatization according to the states of plantlets based on experience and judgment. Moreover, the perlite used for acclimatization must be disposed of due to contamination with pathogens, spreading of pathogens, excessive residual nutrients, and the like, and thus is a new environmental contaminant.

The soft rot and withering occur due to changes in growth environment and the nature of in vitro-cultured plantlets. Since the in vitro culture system has a relative humidity of 90-100%, in vitro-grown plantlets have poor cuticle wax layers, and have smaller and fewer palisade cells than common plants. Also, due to the high humidity, the stomata on leaves of the in vitro-grown plantlets always remain open, and thus are not functional. Roots and stems have poor vascular connections, and thus in vitro-developed roots possess few or no root hairs. When solid medium-grown seedlings are removed from the in vitro conditions, roots extending into the medium are greatly damaged, and the in vitro-cultured seedlings thus cannot perform fully their original function.

An alternative method of acclimatizing in vitro tissue-cultured plantlets into potato seedlings is based on manufacturing a culture bed using a molded bed of Expanded polystyrene and a plastic container box, planting cultured plantlets in an upper board of the culture bed covered with a black vinyl material to prevent internal leakage, and supplying oxygen to a nutrient solution in a manner of supplying nutrients using an air pump filled with the nutrient solution, thereby producing potato seedlings. However, this method also has practical limitations in the mass production of seed potatoes. Due to the nature of in vitro-cultured plantlets and changes in the growth environment, the cut regions of stem cuttings of potato plantlets rot, stems including growing points wither, and so on, thereby making the plantlets unable to grow. Since in vitro-cultured plantlets utilize the limited nutrients contained in the nutrient solution, they lack specific growth nutrients. For a period of about 30 to 40 days required for the production of potato seedlings from in vitro-cultured plantlets, seedlings shocked by nutrient deficiency must be planted in hydroponic facilities after being diagnosed according to the expressed nutritional disorder symptoms and treated through the supplement of deficient nutrients. However, to shorten the acclimatization and cultivation period, the shocked seedlings are immediately planted in hydroponic facilities, causing growers great loss. Also, since seedlings planted through stem cutting directly take up nutrients contained in the culture bed, they are susceptible to contamination by pathogens and to decay. In this case, all of the growing seedlings must be weeded out or discarded, wreaking havoc on potato crops for that year.

Since technical skill and experience from failure lead to success in the production of potato seedlings from in vitro-cultured plantlets as described above, beginning growers have difficulty in practice obtaining high quality potato seedlings. For this reason, in order to stably obtain potato seedlings, seedling sprouts, which are obtained by breaking the dormancy of seed potatoes having a predetermined size (minitubers) and sprouting the minitubers, are used. The seedling sprouts are convenient for use as potato seedlings for planting due to the following advantage. When minitubers having a size of lower than 5 g, which are difficult to seed directly in field of in vitro-produced artificial seed potatoes and hydroponically grown seed potatoes, are dormancy broken, allowed to sprout and grow to about 7-8 cm in stem height in a sterile medium (perlite), and immediately planted as seedlings for planting in hydroponics after mother potatoes are removed therefrom, they can be immediately planted as young seedlings in hydroponics without the complicated acclimatization process required for in vitro-cultured plantlets.

However, there are drawbacks with the use of seedling sprouts. Since minitubers, like general potatoes, have various degrees of dormancy and dormancy periods according to the cultivar, they must be used after conducting the cumbersome process of dormancy breaking. Also, when seedling sprouts are generated using perlite and bed soil, they are susceptible to viral contamination and other major diseases in seed potatoes, leading to lower quality than initial tissue cultured-seedlings. Further, when minitubers to be used to generate seedling sprouts have poor or uncertified quality, they are unable to be used as potato seedlings.

It is also important to produce potato seedlings which are tall and have many nodes on which stolons are formed in order to produce potato seedlings suitable for hydroponics.

The cultivation method of producing seed potatoes by culturing potato seedlings using a nutrient solution is based not on immersing potato seedlings in the nutrient solution or culturing them in perlite or bed soil, but on planting potato seedlings in the air by hanging them on a hollow Expanded polystyrene culture bed. Since potato seedlings are inserted into slits formed on the side surface of a sponge in an up to down direction and pushed along with the sponge into planting holes on the upper board of a culture bed. In the case of weak or over-grown potato seedlings, even when growers with much planting experience transplant potato seedlings, even carefully, the planted seedlings are easily broken and bent inside the sponge, eventually withering and dying. Further, since the planted seedlings do not wither due to water contained therein although they are caught in the sponge, growers cannot find such seedlings. When such seedlings wither, wilt or die due to water loss in the external environment as time goes, the growers find seedlings shocked by environmental stresses caused by planting states, and replant seedlings to replace the shocked seedlings with new seedlings. Thus, a lot of labor and many potato seedlings are required and wasted for replanting for a period ranging from the planting date to the day on which a desired stand of seedlings is established. Also, due to the uneven growth rates according to different rooting time for the growing potato seedlings and the newly planted potato seedlings, required nutrient concentrations and solution supply differ, and some seedlings display immature growth when converted to the reproductive growth period, resulting in low stolon generation. The resulting low tuber formation reduces overall yields and prolongs growth periods, thereby imposing a burden on growers, to perform cultivation management, and causing related stress.

In addition, when produced potato seedlings are short, few or no stem nodes are exposed to the root zone below a culture bed due to the thickness of the upper board of the culture bed, which serves to support potato seedlings, and the thickness of the sponge into which seedlings are inserted. Thus, planted seedlings have lower opportunity for rooting and stolon generation, resulting in decreased yields of seed potatoes. This is because the upper board of the compressed Expanded polystyrene culture bed through which planting holes are formed is about 5 cm thick, and the sponge into which the seedlings are planted in a state of being inserted thereinto has the same thickness of 5 cm as the compressed Expanded polystyrene culture bed, or is slightly thicker.

Thus, it becomes more important to produce seedlings having long stems and many nodes, in which stolons, from which potatoes hang, are generated, the nodes exposed to the root zone below the culture bed except for the thickness of the sponge for planting. Such potato seedlings may be produced by over-growing seedlings in a tender state in a dark room after being acclimatized, or by increasing the growth space. The former solution has the following problems. Seedlings have tender stems due to low light levels and thus bend and fall over due to their weight when grow past a certain level. Since such seedlings are easily broken or bent inside the sponge when planted in facilities, they grow poorly or die, leading to low survival rates and poor seedling establishment. In the case of the latter, since the extended space enables sufficient photosynthesis, uniformly grown seedlings, which have an inverted triangular or diamond-shaped appearance of being short in plant height and having strong stems and short nodes, are obtained, thereby ensuring stable rooting. However, the latter method is also problematic in that it does not guarantee a desired number of stolons through the establishment of a sufficient number of nodes because the hydroponics method employs sponges. In contrast, when seedlings are over-grown and thus appear to have a high enough node number to be able to form the maximal number of stolons, stems are hollow and angular, and thus change to nodes which are unable to form stolons from which potatoes will hang, and generate leaves and stems instead.

Therefore, there is an urgent need for the development of a method of mass producing high quality potato seedlings suitable for the mass production of seed potatoes in hydroponics.

SUMMARY OF THE INVENTION

Accordingly, the present invention has been made keeping in mind the above problems occurring in the prior art, and an object of the present invention is to provide a method of rapidly mass producing disease-free potato seedlings having improved survival rates and rooting when planted by preventing soft rot and rot in the root zone.

Another object of the present invention is to provide a method of mass producing seed potatoes using potato seedlings produced according to the above method.

In order to accomplish the above objects, the present invention provides a method of mass producing potato seedlings, comprising a culturing step of collecting growing points of seed potatoes and culturing the growing points in a liquid or solid medium; a solid culture step of introducing in vitro plantlets obtained from the culture of the growing points to a solid culture; and a deep-flow-stem-cutting-and-acclimatization (DSCA) step of removing the in vitro plantlets from the solid culture and planting the in vitro plantlets through stem cutting and acclimatizing them in deep flow culture in which a nutrient solution is circulating.

The present invention also provides a method of mass producing seed potatoes, comprising planting the potato seedlings produced according to the above method in hydroponic facilities; maximizing the number of stolons by carrying out stem descending work for the planted potato seedlings two or three times; and harvesting potato minitubers formed at the stolons.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION

Figure 1:
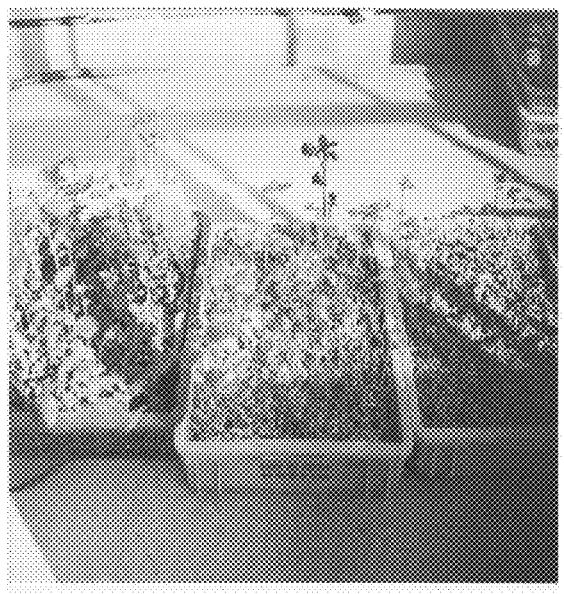
FIG. 1 is a photograph showing potato seedlings grown according to a conventional method using hydroponically grown seed potatoes, dormancy of which broken, and which are sown in perlite culture and allowed to sprout.
Figure 2:
FIG. 2 is a photograph showing potato seedlings for planting in hydroponics, grown according to a conventional method, wherein artificial seed potatoes and hydroponically grown seed potatoes having a size of lower than 5 g are allowed to sprout and grow.
Figure 3:
FIG. 3 is a photograph showing damage due to contamination upon tank culture among conventional methods of producing potato seedlings using in vitro-cultured plantlets.
Figure 4:
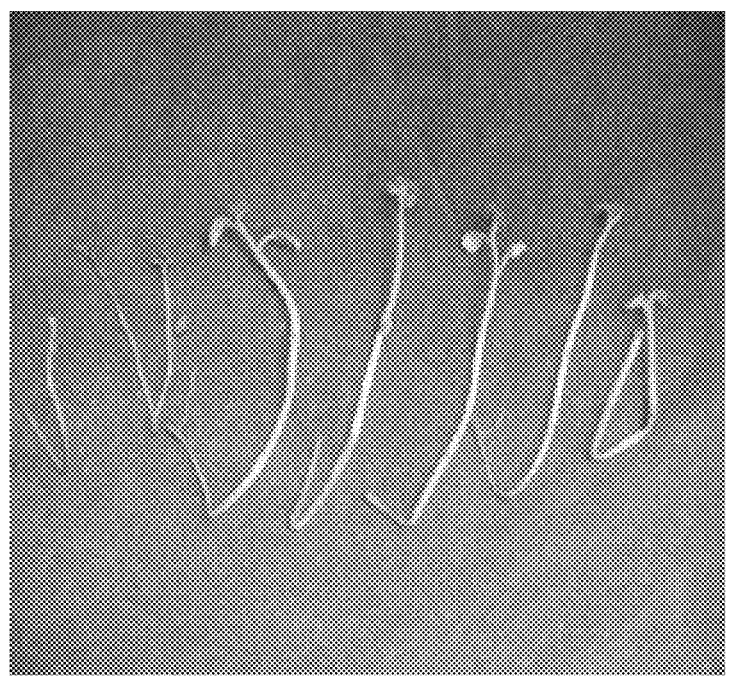
FIG. 4 is a photograph showing the development of soft rot in stem cuttings when in vitro-cultured plantlets are acclimatized and planted through stem cutting to produce potato seedlings for planting in hydroponics according to a conventional method.
Figure 5:
FIG. 5 is a photograph showing grafted and surviving potato seedlings when in vitro-cultured plantlets are acclimatized under external conditions and planted through stem cutting in perlite culture according to a conventional method.
Figure 6:
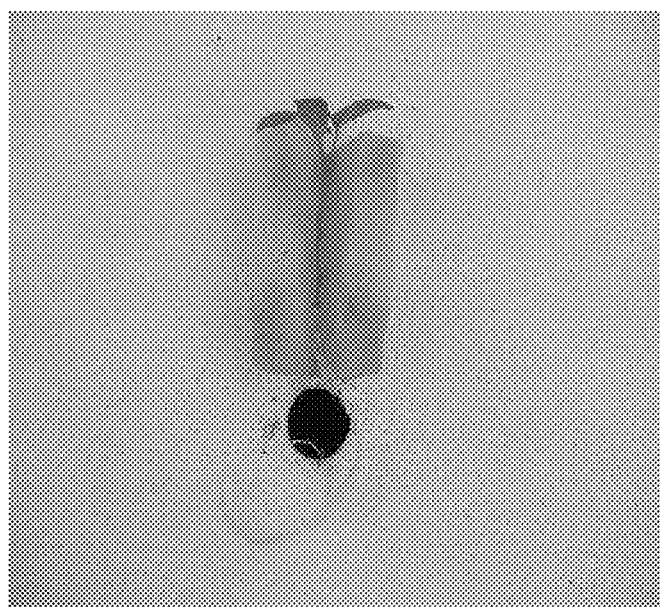
FIG. 6 is a photograph showing a short potato seedling which is inserted into a planting sponge in hydroponic facilities for producing seed potatoes according to a conventional method.
Figure 7:
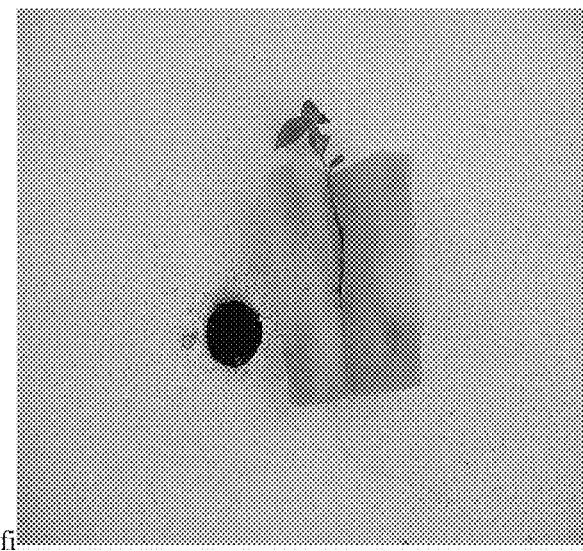
FIG. 7 is a photograph showing a potato seedling the stem of which is broken when inserted into a planting sponge for planting in hydroponic facilities for producing seed potatoes according to a conventional method.
Figure 8:
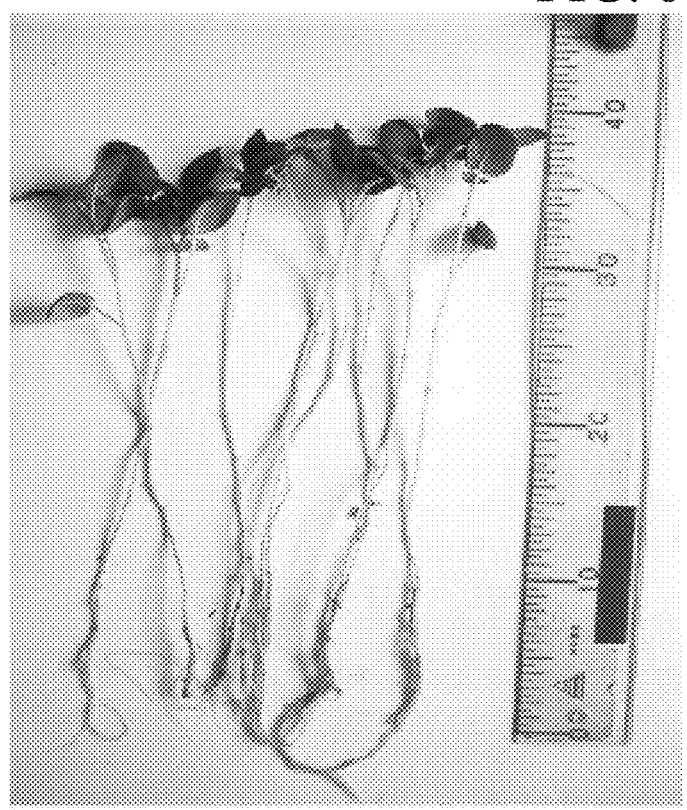
FIG. 8 is a photograph showing Superior potato seedlings produced using in vitro-cultured plantlets according to the present invention, wherein cuttings collected from the in vitro-cultured plantlets sprouted in DSCAC are replanted in SSCAC through stem cutting, and are subjected to stem descending work.
Figure 9:
FIG. 9 is a photograph showing Superior potato seedlings grown in hydroponic facilities according to the present invention, wherein the potato seedlings are produced using DSCAC and SSCAC according to the present invention and planted in hydroponic facilities.
Figure 10:
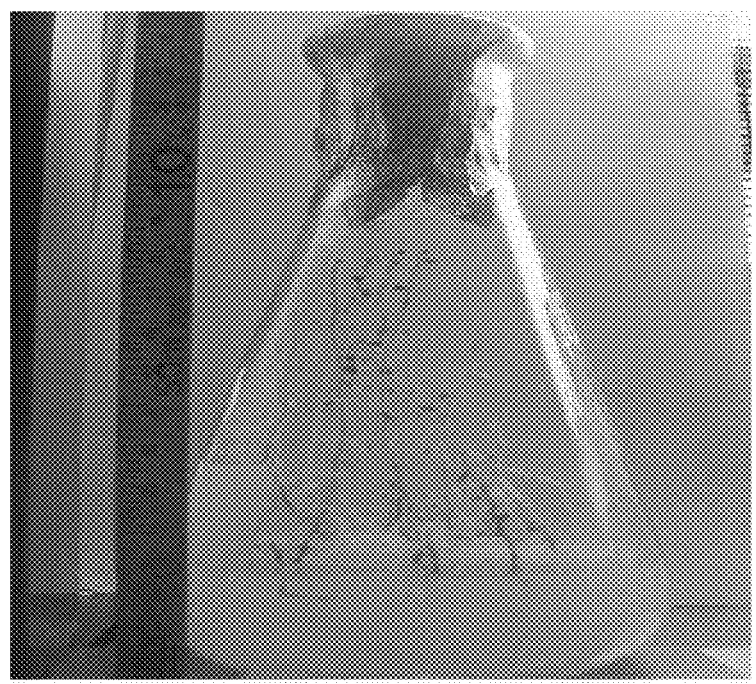
FIG. 10 is a photograph showing in vitro plantlets grown from growing points of Superior potatoes according to the present invention, wherein the growing points are grown in a basic MS medium of pH 5.8, which is supplemented with 80 g/L of sucrose and 9 g/L of agar, at 21° C. under 4,500 Lux lighting for 18-20 hrs, and 0 Lux for 4-6 hrs for 25 days.
Figure 11:
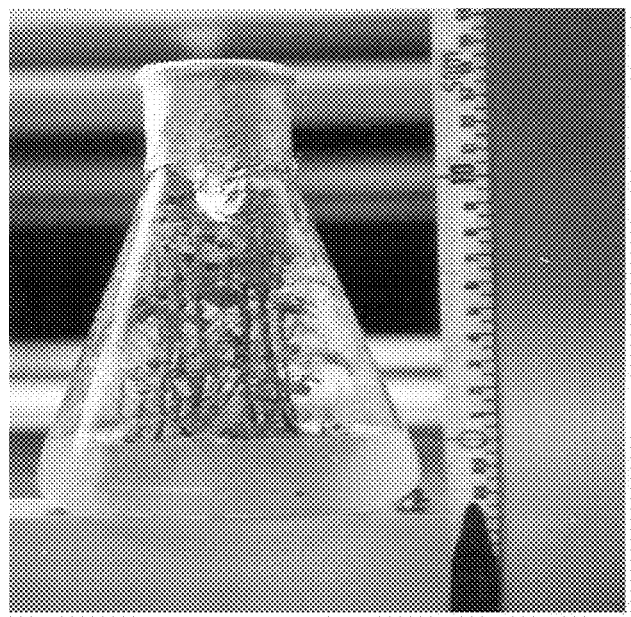
FIG. 11 is a photograph showing in vitro plantlets grown from growing points of Superior potatoes according to the present invention, wherein the growing points are grown in a basic MS medium of pH 5.8, which is supplemented with 80 g/L of sucrose, 0.025 mg/L of coumarin and 9 g/L of agar, at 21° C. under 4,500 Lux lighting for 18-20 hrs, and 0 Lux for 4-6 hrs for 25 days.
Figure 12:
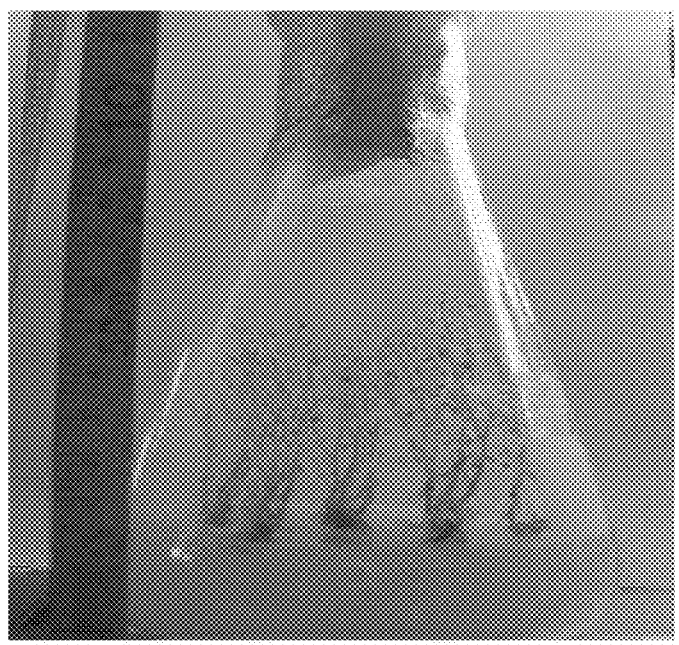
FIG. 12 is a photograph showing in vitro plantlets grown from growing points of Superior potatoes according to the present invention, wherein the growing points are grown in a basic MS medium of pH 5.8, which is supplemented with 2 g/L of hyponex, 80 g/L of sucrose and 9 g/L of agar, at 21° C. under 4,500 Lux lighting for 18-20 hrs, and 0 Lux for 4-6 hrs for 25 days.
Figure 13:
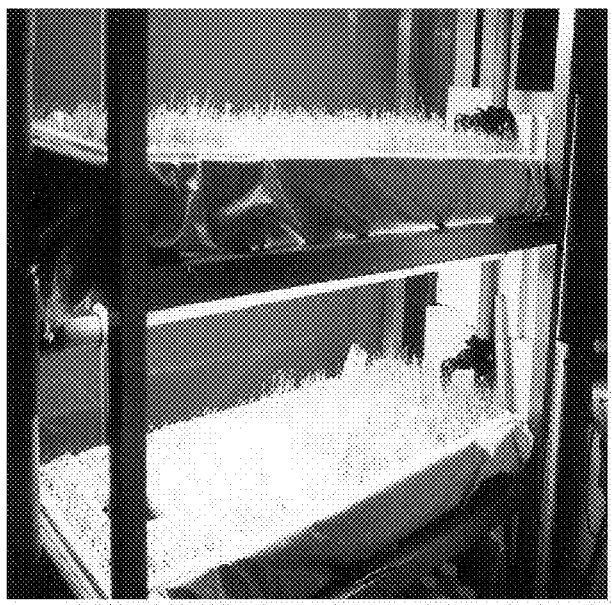
FIG. 13 is a photograph showing potato seedlings produced using in vitro-cultured plantlets, wherein the plantlets are planted in DSCAC through stem cutting and stimulated to generate terminal and lateral buds under dark conditions according to the present invention.
Figure 14:
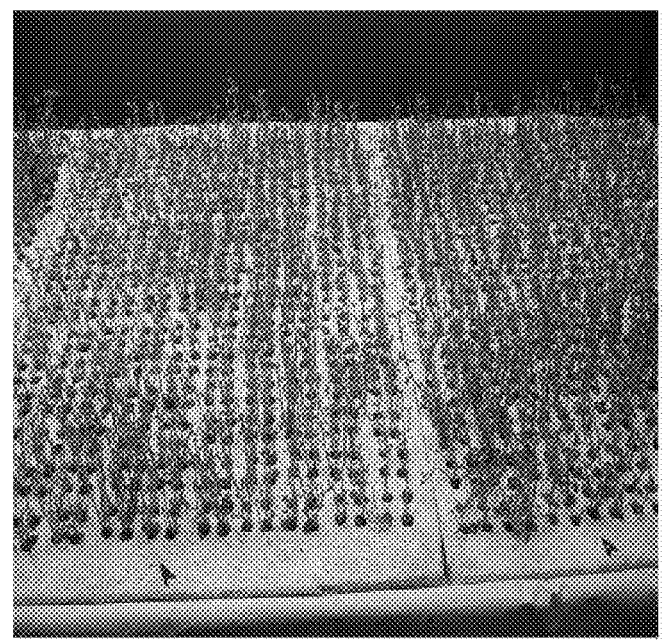
FIG. 14 is a photograph showing potato seedlings, wherein sprouts (shoots) from the terminal and lateral buds generated in the dark are hardened by controlled radiation in which the light intensity is gradually increased according to the present invention.
Figure 15:
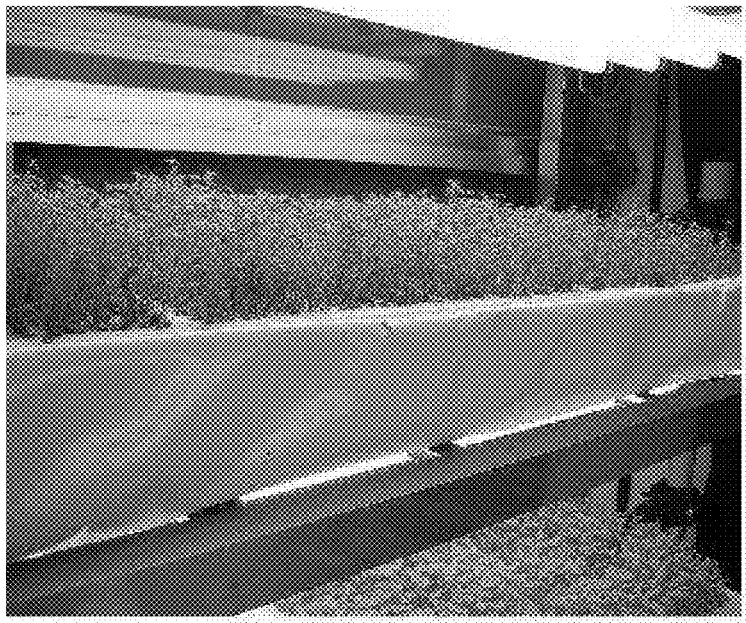
FIG. 15 is a photograph showing potato seedlings produced using in vitro-cultured plantlets, wherein the plantlets are planted in DSCAC through stem cutting and are allowed to grow for 13 days according to the present invention.
Figure 16:
FIG. 16 is a photograph showing the large-scale collection of potato seedlings grown in DSCAC according to the present invention and having a size of more than 5 cm to be used as potato seedlings for replanting through stem cutting.
Figure 17:
FIG. 17 is a photograph showing potato seedlings for replanting through stem cutting collected from DSCAC according to the present invention.
Figure 18:
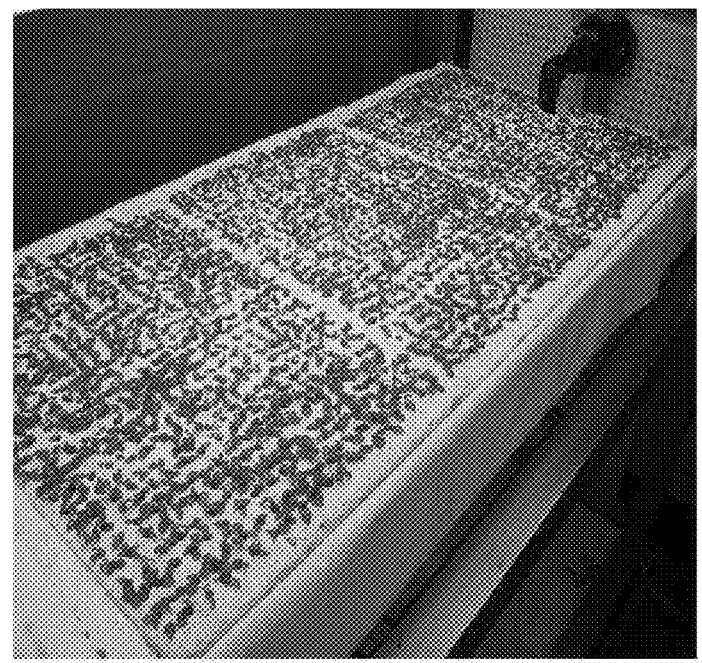
FIG. 18 is a photograph showing potato seedlings replanted in DSCAC through stem cutting according to the present invention.
Figure 19:
FIG. 19 is a photograph showing potato seedlings for replanting through stem cutting, which are collected from DSCAC, wherein the seedlings are replanted in DSCAC through stem cutting and then grown for 10 days, according to the present invention.
Figure 20:
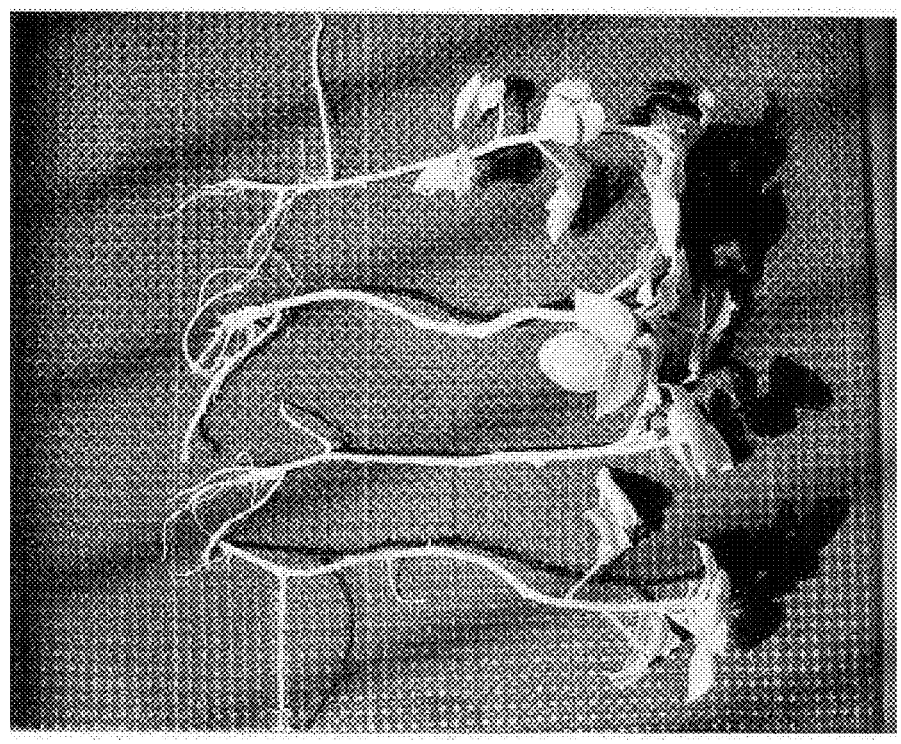
FIG. 20 is a photograph showing potato seedlings for replanting through stem cutting, which are collected from DSCAC, wherein the seedlings are replanted in DSCAC through stem cutting and then allowed to grow for 10 days, according to the present invention.
Figure 21:
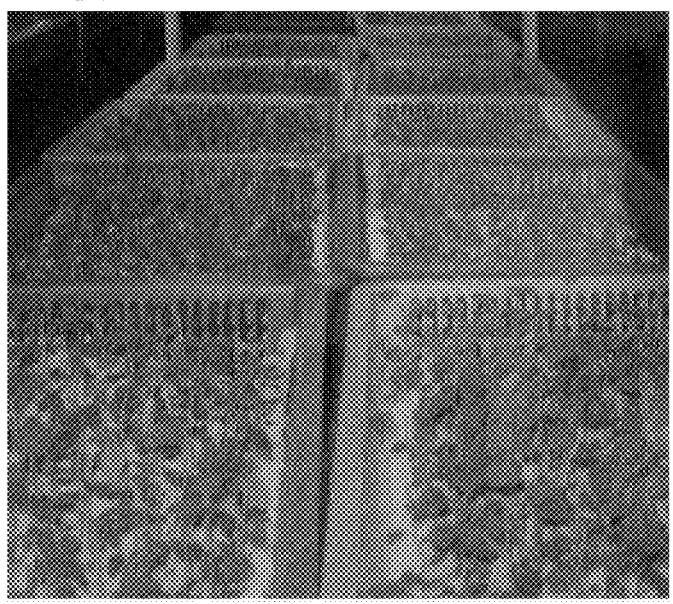
FIG. 21 is a photograph showing potato seedlings for replanting through stem cutting, which are collected from DSCAC, wherein the seedlings are replanted in perlite culture through stem cutting and then grown for 10 days according to the present invention.
Figure 22:
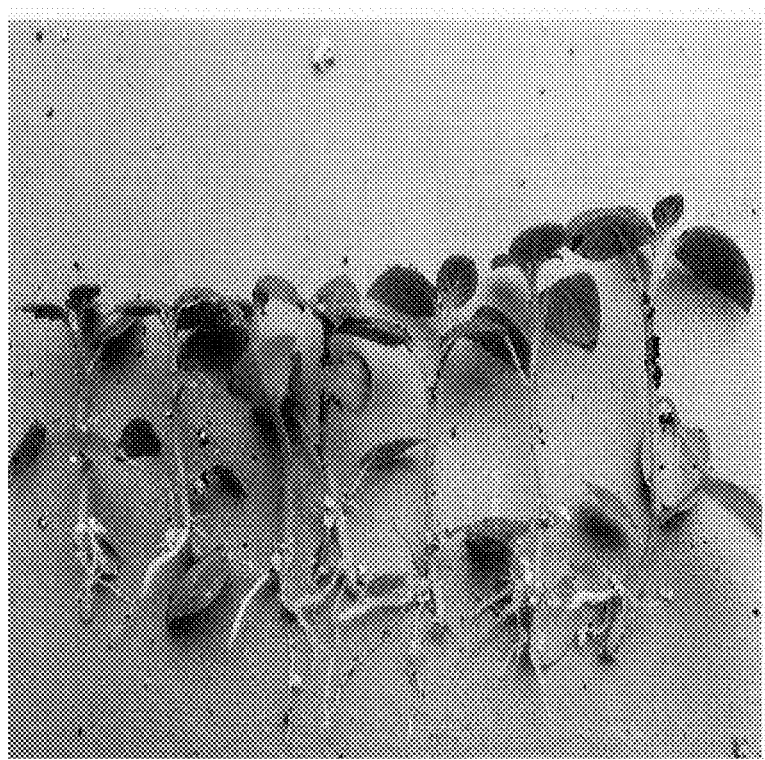
FIG. 22 is a photograph showing potato seedlings for replanting through stem cutting, which are collected from DSCAC, wherein the seedlings are replanted in perlite culture through stem cutting and then grown for 15 days, according to the present invention.
Figure 23:
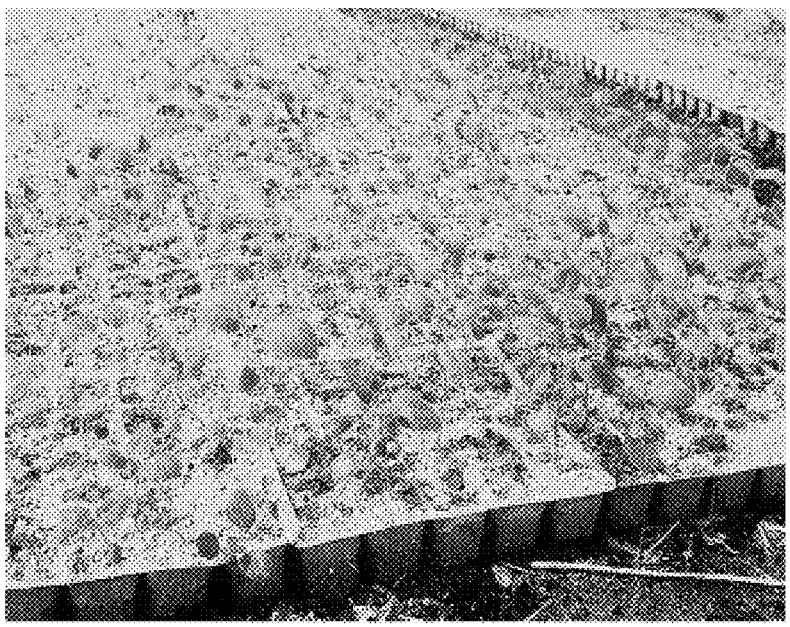
FIG. 23 is a photograph showing potato seedlings for replanting through stem cutting, which are collected from DSCAC, wherein the seedlings are replanted in perlite culture through stem cutting to be used as potato seedlings for general soil culture, hardened, and grown for 10 days, and transplanted into a plug tray filled with sterile bed soil and grown for 10 days according to the present invention.
Figure 24:
FIG. 24 is a photograph showing plug potato seedlings which are planted in a greenhouse and grown for 25 days according to the present method.
Figure 25:
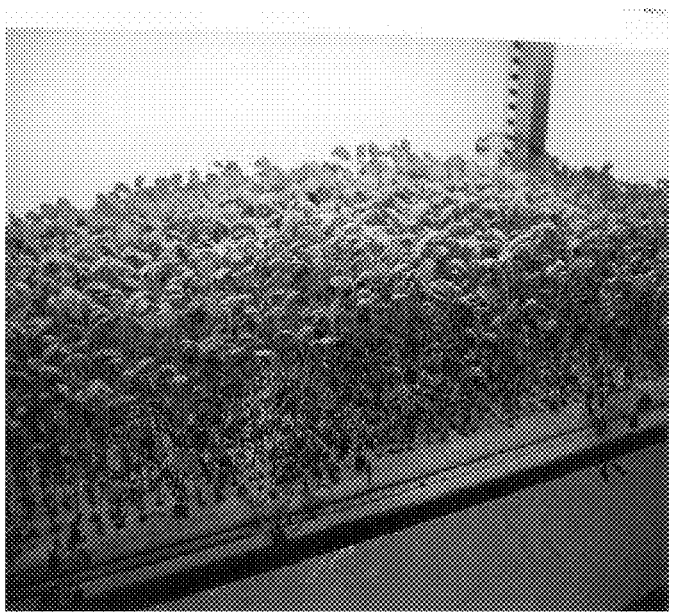
FIG. 25 is a photograph showing potato seedlings for replanting through stem cutting, which are collected from DSCAC, wherein the seedlings are replanted in SSCAC through stem cutting and then grown for 10 days according to the present invention.
Figure 26:
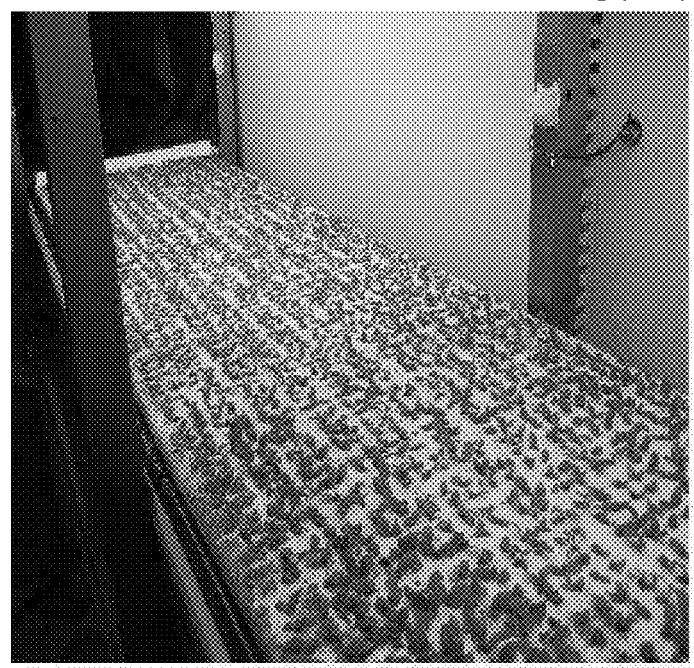
FIG. 26 is a photograph showing potato seedlings which are stem-descended in SSCAC according to the present invention.
Figure 27:
FIG. 27 is a photograph showing potato seedlings for planting in hydroponics, which are grown through DSCAC and SSCAC according to the present invention.
Figure 28:
FIG. 28 is a photograph showing a potato seedling which has grown vigorously by taking up nutrients and water due to rapid root development when cut to remove three quarters of the roots after being produced through SSCAC and planted in hydroponic facilities for producing seed potatoes according to the present invention.
Figure 29A:
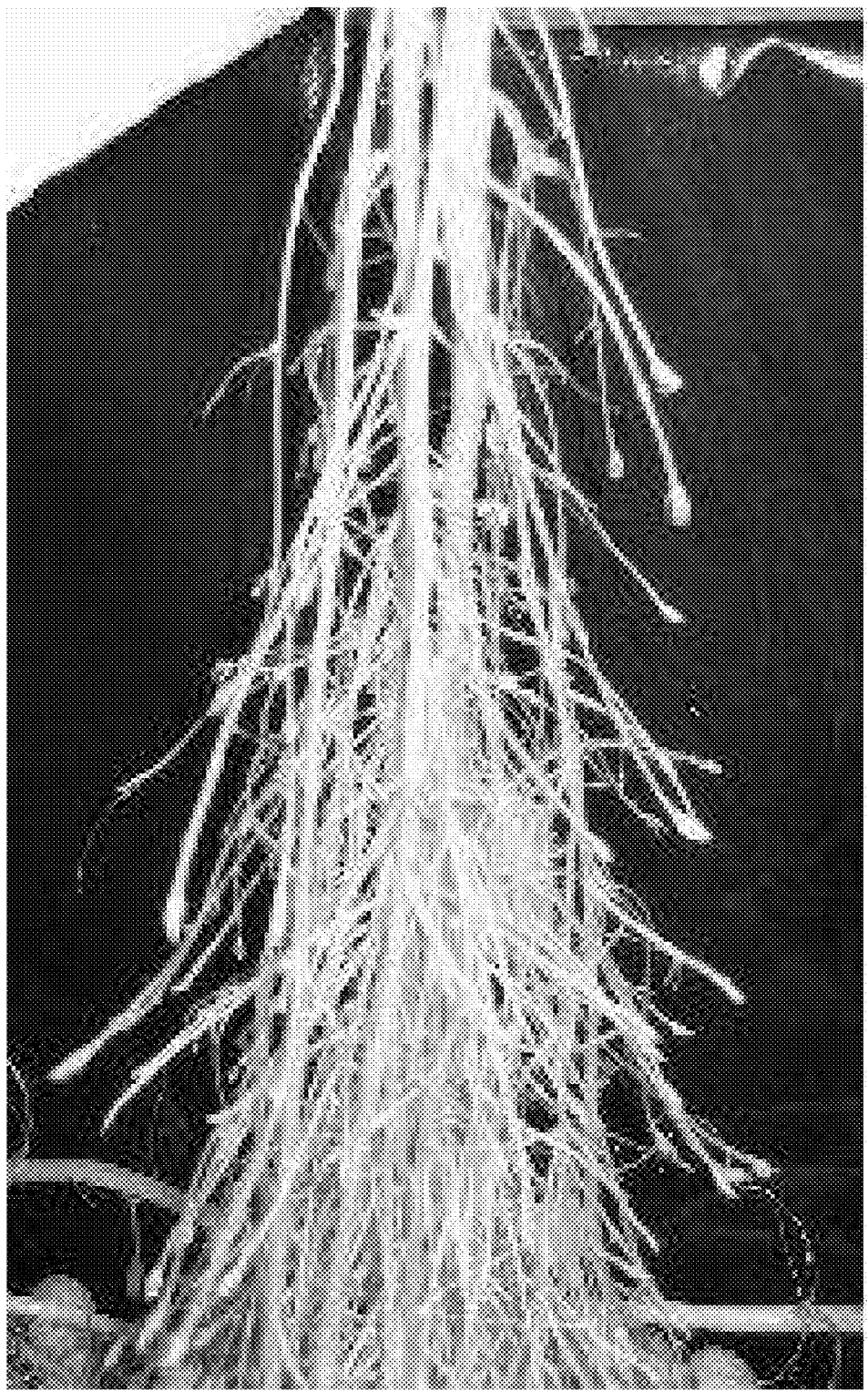
FIGS. 29a and 29b are photographs showing the tubers formed by the emergence of primary, secondary and tertiary stolons, on which potatoes hang up to the end of upper nodes of stems of seed potatoes when potato seedlings produced according to the present invention are planted and cultivated in hydroponic facilities.
Figure 29B:
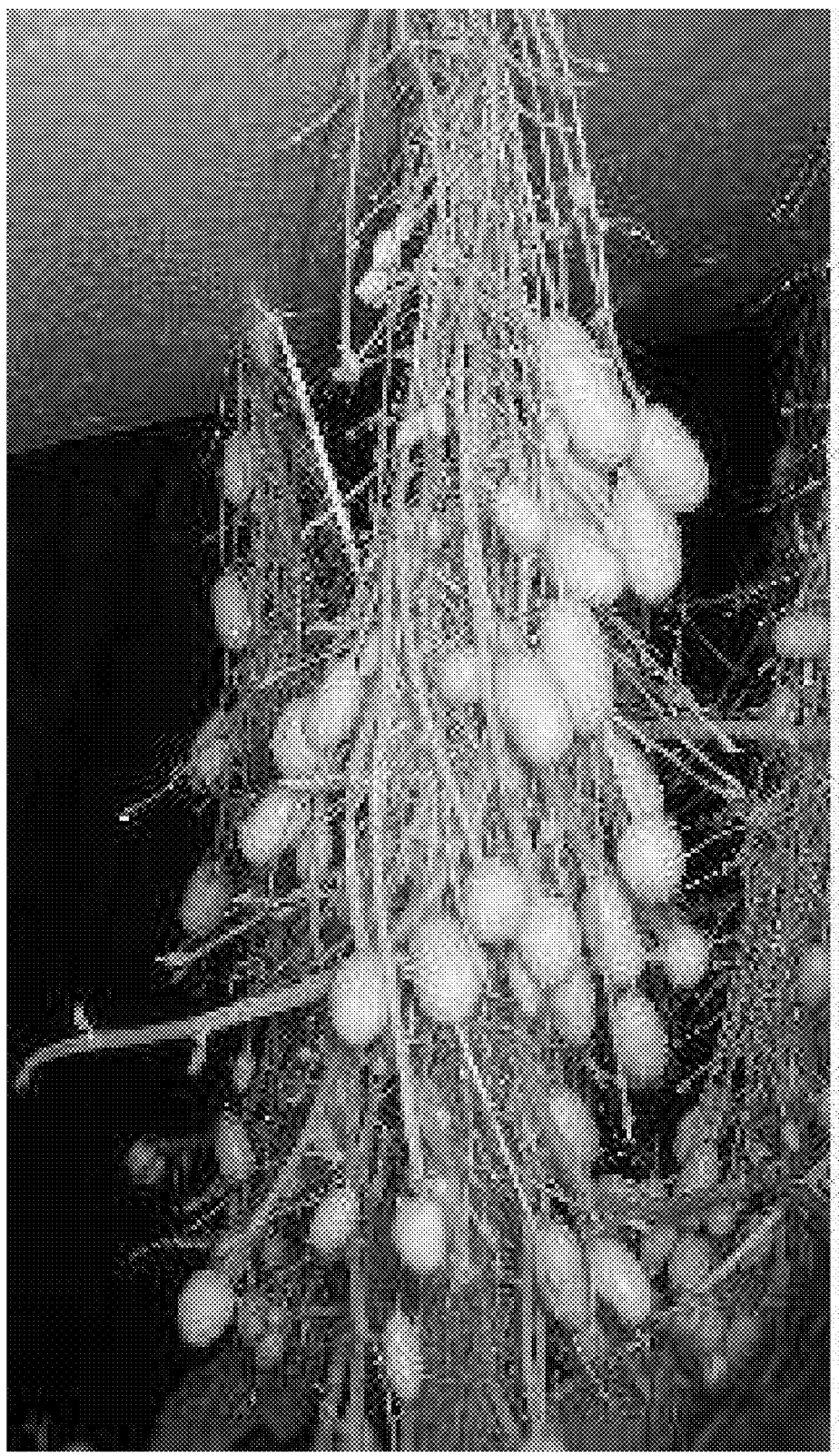

Terms used herein are defined as follows.

The term "deep-flow-stem-cutting-and-acclimation" (hereinafter abbreviated to as "DSCA"), as used herein, refers to a process of planting through stem cutting and cultivating tissue-cultured potato seedlings in deep flow culture, in which a nutrient solution is circulated.

The term "spraying-stem-cutting-and-acclimation" (hereinafter abbreviated to as "SSCA"), as used herein, refers to a process of cultivating potato seedlings by spraying a nutrient solution to the root zone of potato seedlings through nozzles.

The term "deep-flow-stem-cutting-and-acclimation-culture" (hereinafter abbreviated to as "DSCAC"), as used herein, refers to an apparatus in which the DSCA is performed.

The term "spraying-stem-cutting-and-acclimation-culture" (hereinafter abbreviated to as "SSCAC"), as used herein, refers to an apparatus in which the SSCA is performed.

The present invention provides a method of mass producing potato seedlings, comprising a culturing step of collecting growing points of seed potatoes and culturing the growing points in a liquid or solid medium; a solid culture step of introducing in vitro plantlets obtained from the culture of the growing points to a solid culture; and a DSCA step of removing the in vitro plantlets from the solid culture and planting through stem cutting and acclimatizing the in vitro plantlets in deep flow culture, in which a nutrient solution is circulated.

In the method of mass producing potato seedlings according to the present invention, the collected growing points may be cultured in a solid medium or a liquid medium. Liquid culture in a rotary shaker is preferred.

The growing points of seed potatoes are preferably cultured for a period ranging from 24 to 26 days at 18-22° C. under 900-1,100 Lux lighting for 18-20 hrs, and 0 Lux for 4-6 hrs in a basic MS medium of pH 5.7-5.8 supplemented with 28-32 g/L of sucrose, or in such a medium further supplemented with 7-11 g/L of agar.

Preferably, the method further includes performing pathogen testing for the in vitro plantlets after the growing points of seed potatoes are cultured. After the step of detecting viral infections or other diseases, potato seedlings identified as disease-free are selected and mass produced, thereby enabling the mass production of disease-free potato seedlings, which are not infected with viruses or other diseases. Available disease identification methods are not specifically limited, but six species of viruses are preferably detected in each individual using ELISA.

The solid culture is preferably composed of two sub-steps: primary shoot subculture and secondary propagation culture.

The primary shoot subculture is carried out preferably in a basic MS medium of pH 5.7-5.8, which is supplemented with 7-11 g/L of agar and 70-80 g/L of sucrose, and more preferably in a basic MS medium supplemented with 9 g/L of agar and 80 g/L of sucrose. The secondary propagation culture is carried out preferably in a basic MS medium of pH 5.7-5.8, which is supplemented with 7-11 g/L of agar, 70-80 g/L of sucrose and 0.020-0.035 mg/L of coumarin, and more preferably in the basic MS medium supplemented with 9 g/L of agar, 80 g/L of sucrose and 0.025 mg/L of coumarin.

Since plant cells growing in vitro usually have lowered photosynthetic activity, they should receive a carbon source from the culture medium in order to get the energy required for cellular carbon skeleton manufacture and metabolism. Taking into account the property of tissue culture undergoing a sterilization process (1.2 atm, 124° C.), sucrose, which is relatively stable at high temperatures, is preferred. The sucrose added to the medium is taken up as an energy source for culture cells by plantlets, and thus affects cellular proliferation and growth as well as being involved in the redifferentiation of plantlets. When sucrose is present in a large amount of 80 g/L, the best growth of potato seedlings is achieved.

In order to cultivate in vitro plantlets into potato seedlings having robust and elastic stems through exposure to the external dry environment, a large amount of carbohydrates should be accumulated inside the plantlets even though light levels are low. For this, sucrose is most preferably used in an amount of 70-80 g/L. When sucrose is present in an amount lower than 70 g/L, no robust potato seedlings are obtained. When the amount of sucrose exceeds 80 g/L, reverse osmosis occurs in the opposite direction of root pressure for nutrient absorption, thus no carbohydrates are accumulated.

The primary shoot subculture and the secondary propagation culture are individually carried out preferably for 25-35 days at 4,000-5,000 Lux, for 18-20 hrs, and 0 Lux for 4-6 hrs and more preferably for 30 days at 4,500 Lux for 18-20 hrs, and 0 Lux for 4-6 hrs.

After the secondary propagation culture, the potato seedlings are removed, and may be immediately subjected to DSCA, or subjected to DSCA after being acclimatized. It is preferable to shorten the production period so that the potato seedlings do not immediately undergo the acclimatization process but are immediately planted through stem cutting in deep flow culture and then acclimatized.

Since tissue-cultured seedlings have been grown under in vitro closed conditions having high humidity and low light levels, they have low growth rates, long internodes and thin stems. In order to be transplanted to a greenhouse or a hydroponics operation under dry conditions at high light levels, the tissue-cultured seedlings must be able to survive the stresses of the external environment. For this, they must undergo an acclimatization process, in which the culture environment of the in vitro plantlets is gradually changed to resemble the external environment. However, the acclimatization process is carried out for a long period ranging from about 10 to 15 days. Also, in spite of being acclimatized, in vitro plantlets have varying survival rates according to the experience and ability of growers, and the desired quality of seedlings may vary depending on growers. Therefore, as described in the present invention, it is very important to produce potato seedlings suitable in the external environment from in vitro plantlets for a shorter period through the DSCA step, without requiring a separate acclimatization process.

The potato seedlings planted in the DSCA step through stem cutting have stems from which all of the leaves have fallen. Preferably, the stems are slightly old and thus are hardened. In the case in that potato seedlings actively grown in vitro (for 30-35 days) are removed and planted through stem cutting, since soft stems thick with leaves but having no roots are cut and planted, the leaves wither due to overpropagation, and plantlets wilt and die, or have low rooting rates due to severe fatigue. When in vitro-cultured seedlings are removed in a state in which leaves are fallen and only stems remain and are then planted, 100% success is realized.

The potato seedlings to be planted in the DSCA step through stem cutting are preferably cut at node regions at a lower part of stems with a disinfected sharp knife. Preferably, the seedlings are cut in only one attempt. The DSCA step is preferably carried out with a nutrient solution of pH 6.6-7.0 at a temperature of 18-22° C. Preferably, the light intensity is gradually increased according to the growth phase in order to gradually harden potato seedlings. Most preferably, the light intensity is a) 0 Lux for 55-65 hours→b) 2,100 Lux for 45-55 hours, 0 Lux for 4-8 hours→c) 3,600 Lux for 35-45 hours, 0 Lux for 4-8 hours→d) 5,500 Lux for 25-35 hours, 0 Lux for 4-8 hours→e) 7,000 Lux for 535-545 hours (lighting for 18-20 hours every day for 30 days), 0 Lux for 120-180 hours (dark condition for 4-6 hours every day for 30 days).

After the stem cuttings have been planted, they are first incubated under dark conditions for a period of 55-65 hrs in order to generate white shoots. Since most plantlets take up nutrients dissolved in water by the adhesion of water molecules resulting from transpiration through ground parts, the shoots primarily generated at terminal and lateral buds stimulate the generation of root hairs, which are able to absorb nutrients and water into the planted root-zone stem cuttings. This ensures the survival of in vitro-cultured plantlets with questionable viability. Also, when sprouts from the terminal and lateral buds of plantlets are hardened by gradually increasing light levels from the dark condition, the plantlets have healthy dark-green leaves and a high accumulation of carbohydrates, thereby having a good appearance, robust and not over-grown stems, and elastic and short nodes.

In the DSCA step, it is preferable that the supply of a nutrient solution and the interruption of the nutrient solution supply be repeatedly alternated. Preferably, the nutrient solution is supplied for 30-45 min, and the supply of the nutrient solution is then interrupted for 90-180 min. This is because the frequent supply of the nutrient solution leads to good growth of potato seedlings but brings about soft rot due to excessive water uptake, and wilt occurs due to water evaporation from seedlings when the nutrient solution is not supplied for a long period of time.

When the nutrient solution is supplied, it is preferable that the nutrient solution flow without fluctuation on the surface thereof and be supplied at a constant level. This is because rapid flow and swirling, which are caused by water pressure generated from the supplied nutrient solution, stress potato seedlings planted through stem cutting, and thus inhibit rooting and growth.

When the supply of the nutrient solution is interrupted, it is preferable that the supplied nutrient solution and growth debris be completely discharged to expose stems and roots of potato seedlings to the air. That is, the roots of potato seedlings are completely exposed to the air, and air influxes and circulates through holes for planting of stem cuttings, which are formed in a culture panel, thereby preventing soft rot and root rot due to over-immersion and excessive water uptake of potato seedlings planted through stem cutting.

In the DSCA step, it is preferable that potato seedlings be repeatedly collected from 13-15 days after planting of stem cuttings at time intervals of 6-10 days until nodes are exhausted. This results in a large number of potato seedlings being obtained.

Preferably, the DSCA step is performed with a DSCAC, comprising a culture panel in which holes for planting stem cuttings are arranged to plant potato seedlings through stem cutting and cultivate the seedlings; a culture bed which has a space in which the culture panel is placed, contains a supplied nutrient solution required for the growth of the potato seedlings planted through stem cutting in the culture panel, and has a water outlet for discharging excess supplied nutrient solution; a light source which is provided at one side of the culture bed and radiates light on potato seedlings planted through stem cutting in the culture panel; a nutrient solution dispersion and supply tube which is provided at one side of the culture bed and flows and supplies the nutrient solution to a lower part of the culture bed; and a nutrient solution preparation and supply part which is equipped with a nutrient solution tank, is connected to the nutrient solution dispersion and supply tube and supplies the nutrient solution thereto.

In the DSCAC, the water outlet of the culture bed is provided with a water discharge tube having a slit in a longitudinal direction. Preferably, an opening and closing tube having a helical opening and closing part is inserted into the water discharge tube in a separated state against the lower part of the water discharge tube.

In the DSCAC, the culture bed is formed in two layers by a support frame in which the space in which the nutrient solution is held is formed in two layers. The nutrient solution dispersion and supply tube connected to the nutrient solution tube is placed in the space formed in each layer of the support frame. Fluorescent lamps as the light source are arranged in two rows in the lower part of the culture bed formed in each layer of the support frame. Herein, the nutrient solution dispersion and supply tube in each layer is connected to one side of the support frame to supply the nutrient solution. A main supply tube having a flow control valve for controlling the amount of inflowing nutrient solution is placed between the nutrient solution dispersion and supply tubes. The main supply tube is placed in an upright form such that it extends to the upper part of the culture bed placed at the uppermost part of the support frame. The uppermost part of the main supply tube is larger in volume than the lower part, and is coupled with a pressure tube connected to the nutrient solution tank. A pressure control valve for controlling the pressure against the main supply tube is placed between the main supply tube and the pressure tube.

In the DSCAC, the water outlet of the culture bed preferably includes a discharge tube which is connected to the nutrient solution tank and recovers the discharged nutrient solution into the nutrient solution tank. Preferably, a micro-sieving net is placed at a terminal part of the discharge tube to sift sediments or impurities contained in the circulating nutrient solution. This removal of sediments or impurities from the circulating nutrient solution prevents rot and soft rot at the root zone.

In the DSCAC, one side of the nutrient solution dispersion and supply tube is a T-shaped branch tube into which the nutrient solution is supplied from the nutrient solution tank. The branch tube has an effusion tube, in which a nozzle from which the nutrient solution flows out is formed and which is horizontally provided at the lower surface of the culture bed in order to ensure stable flow of the nutrient solution supplied into the planted bed without fluctuation.

In the method of mass producing potato seedlings according to the present invention, the potato seedlings, having undergone the DSCA step, may be collected and replanted through stem cutting in any system, whether DSCAC, perlite culture, or SSCAC. Preferably, after the step of deep-flow-stem-cutting-and-acclimatization, the potato seedlings are subjected to an SSCA step, in which a nutrient solution is sprayed onto the root zone of the potato seedlings through nozzles.

The SSCA step is preferably performed in an SSCAC, comprising a culture panel in which holes for planting stem cuttings are arranged to plant potato seedlings through stem cutting and cultivate them; a culture bed in which the culture panel is supported at an upper part and which has a spray tube having nozzles spraying in a mist form a nutrient solution required for the growth of the potato seedlings planted through stem cutting in the culture panel, and a water outlet for discharging the nutrient solution that has been sprayed and has flowed down; a light source which is provided at one side of the culture bed and radiates light onto potato seedlings planted through stem cutting in the culture panel; and a nutrient solution preparation and supply part which is equipped with a nutrient solution tank in which the spray tube of the culture bed is connected to one side and the nutrient solution is stored.

Preferably, the spray tube has a cleaning valve for discharging sediments contained therein at a terminal part. The culture bed is formed in two layers by a support frame in which the space into which the nutrient solution is sprayed is formed in two layers. The spray tube connected to the nutrient solution tank is placed in the space provided in each layer of the support frame. Herein, the spray tube in each layer is connected to one side of the support frame to supply the nutrient solution. A main supply tube having a flow control valve for controlling the inflowing amount of the nutrient solution is placed between the spray tubes. The main supply tube is placed in an upright orientation such that it extends to an upper part of the culture bed placed at the uppermost part of the support frame. The uppermost part of the main supply tube is larger in volume than the lower part, and is coupled with a pressure tube connected to the nutrient solution tank.

Preferably, the water outlet of the culture bed includes a discharge tube which is connected to the nutrient solution tank and transfers the discharged nutrient solution into the nutrient solution tank. A micro-sieving net is placed at the terminal part of the discharge tube to sift sediments or impurities introduced into the nutrient solution tank.

The nutrient solution preparation and supply part preferably comprises a stock solution tub which supplies a stock solution containing organic and inorganic nutrients to prepare the nutrient solution of the nutrient solution tank; an acidic solution tub which is provided at one side of the stock solution tub and supplies an acidic solution to the nutrient solution tank to control the acidity of nutrient solution tank; a quantization pump which is connected to the stock solution tub and the acidic solution tub, and receives the stock solution and the acidic solution and supplies them to the nutrient solution tank in predetermined amounts; a temperature control part, which controls the temperature of the nutrient solution by receiving the nutrient solution, heating it and transferring it to the nutrient solution tank; a sensor part, which is equipped with a nutrient solution temperature sensor for measuring the temperature of the nutrient solution stored in the nutrient solution tank, a pH sensor for measuring acidity, and a concentration sensor for measuring the nutrient concentrations of the nutrient solution; and a control part which controls the temperature of the nutrient solution by measuring the temperature of the nutrient solution through the nutrient solution temperature sensor and operating the temperature control part, and controls the amount of the stock solution and the acidic solution supplied to the nutrient solution tank through the quantization pump after checking the temperature, concentration and acidity of the nutrient solution through the pH sensor and the concentration sensor.

The nutrient solution preparation and supply part preferably includes a water level sensor which senses the water level in the nutrient solution tank.

The nutrient solution tank of the nutrient solution preparation and supply part is preferably equipped with a water disinfection part which disinfects the nutrient solution, and a bubble generation part which generates bubbles in the nutrient solution.

Preferably, ultraviolet disinfection parts are placed in a tube connecting the nutrient solution tank and the culture beds in order to disinfect the nutrient solution.

The SSCA step is preferably performed with a nutrient solution of pH 6.6-7.0 at 18-21° C. under 6,500-7,500 Lux for 18-20 hrs, and 0 Lux for 4-6 hrs. The nutrient solution is preferably supplied for 30 sec and interrupted for 4 min.

In the SSCA step, it is preferable that when the aboveground portion of potato seedlings has grown to about 8-12 cm in length, lower leaves except for two to four upper leaves be removed with disinfected scissors, and stem descending work be carried out two or three times by descending the stems of potato seedlings below the culture panel. This work maximizes the number of round nodes from which stolons are generated, thereby maximizing the yield of seed potatoes.

Preferably, the SSCA step is performed during a period ranging from 32 to 40 days, and all lower leaves except for two or three upper leaves are removed during the last 5-7 days. The roots of potato seedlings are cut to remove three quarters thereof, and are then allowed to regenerate. This process improves rooting rates in hydroponic facilities.

Because, when potato seedlings are replanted through stem cutting without the removal of developed roots, rooting occurs after the roots of the potato seedlings planted through stem cutting have disappeared, it takes a longer time to generate new roots, the decay of the previous roots brings about stem soft rot and eventually plant death. When the roots of potato seedlings are completely removed, the leaves and stems wilt due to insufficient water uptake at the root zone, and thus, it takes a longer time for seedlings to root, thereby making the initial growth of seedlings difficult. Thus, when the root regeneration is performed after three quarters of the roots have been cut off, the planted seedlings have improved rooting when planted in hydroponic facilities.

Referring to the accompanying drawings, the construction and operation principle of the DSCAC and SSCAC, in which DSCA and SSCA are carried out, will be described below.

Figure 30:
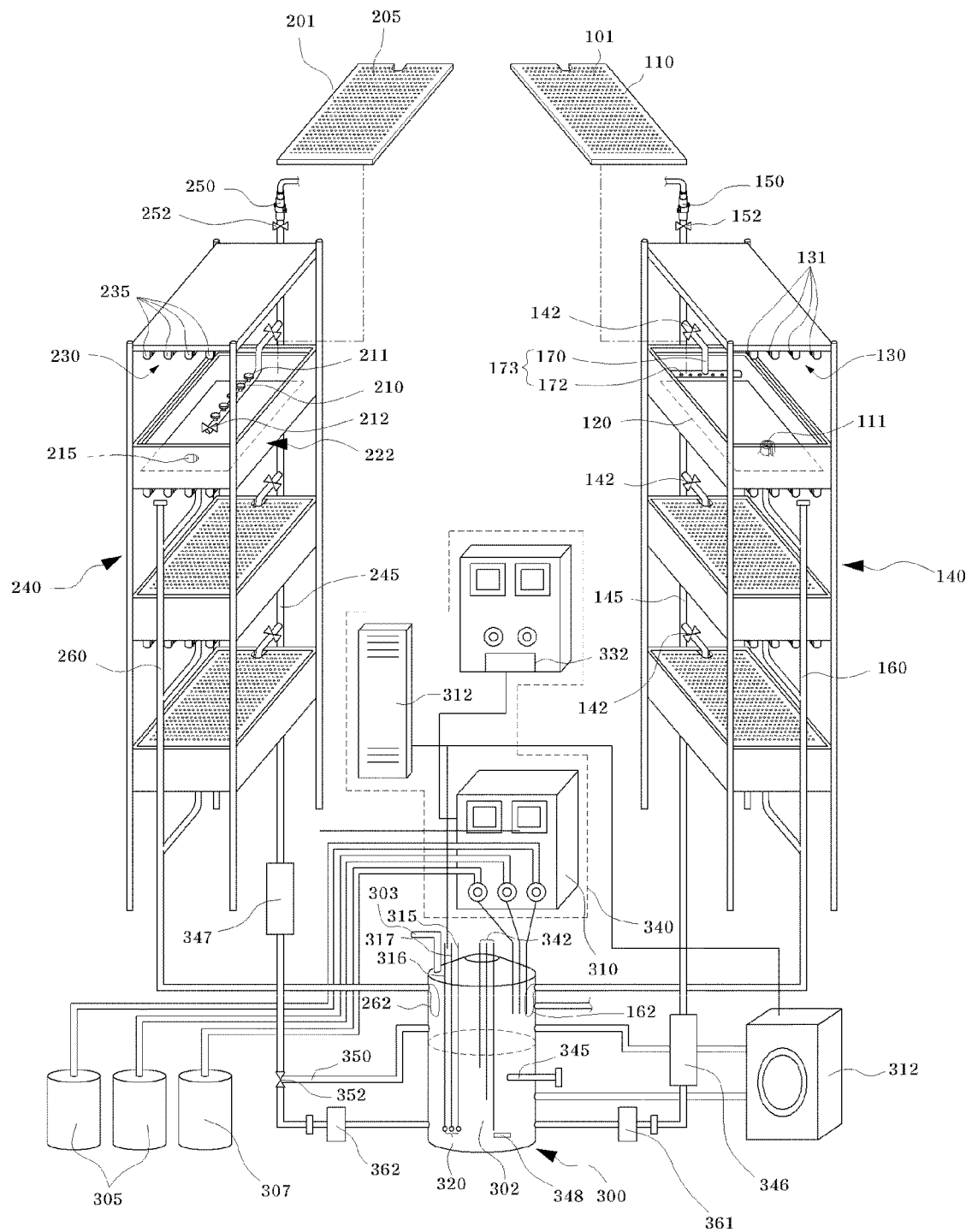
FIG. 30 illustrates the construction of DSCAC and SSCAC used for producing potato seedlings according to the present invention.
Figure 31:
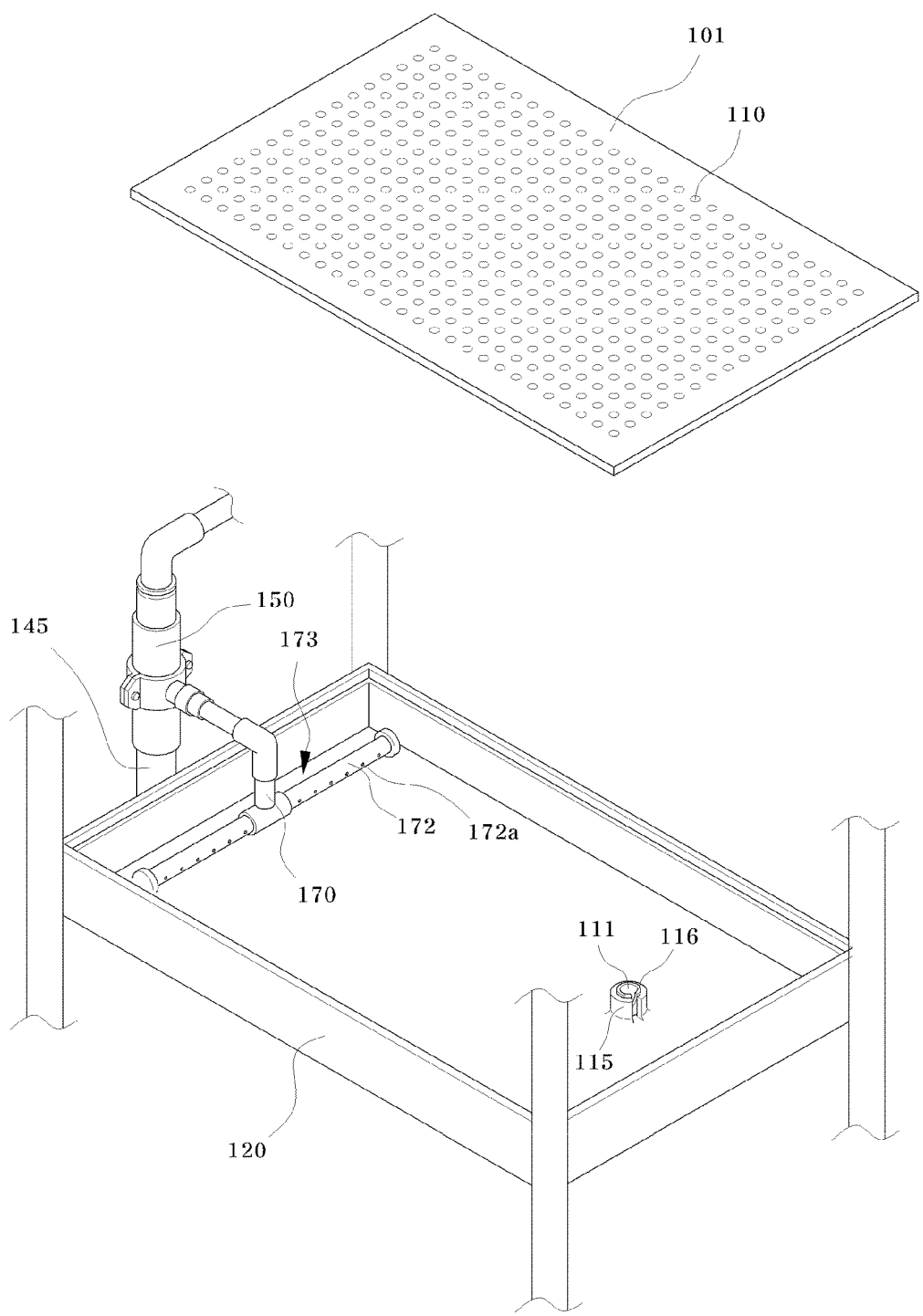
FIG. 31 is a partial perspective view of a culture bed provided in a support frame of DSCAC used for producing potato seedlings according to the present invention.
Figure 32:
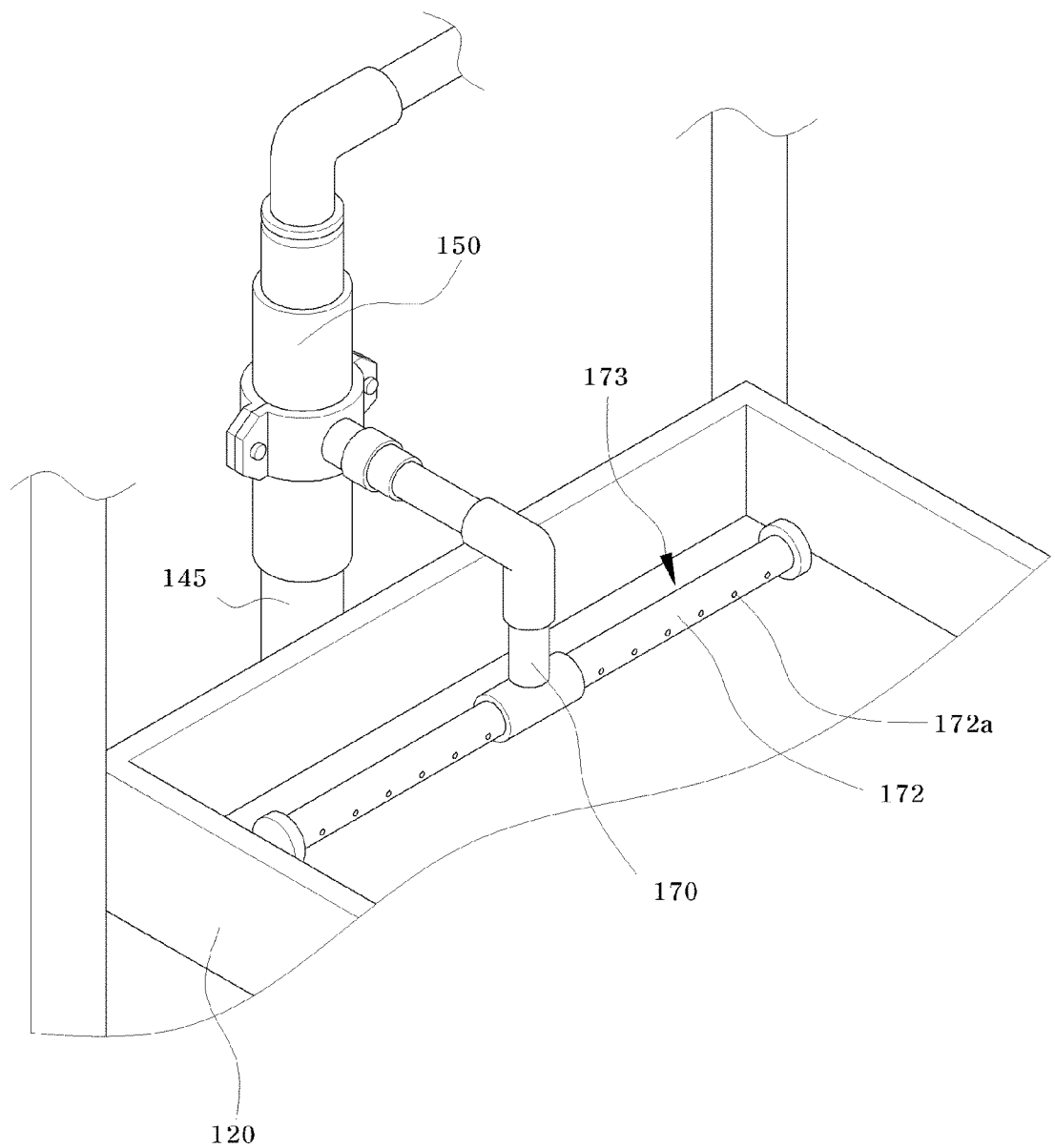
FIG. 32 is a partial perspective view of a culture bed of DSCAC used for producing potato seedlings according to the present invention.
Figure 33:
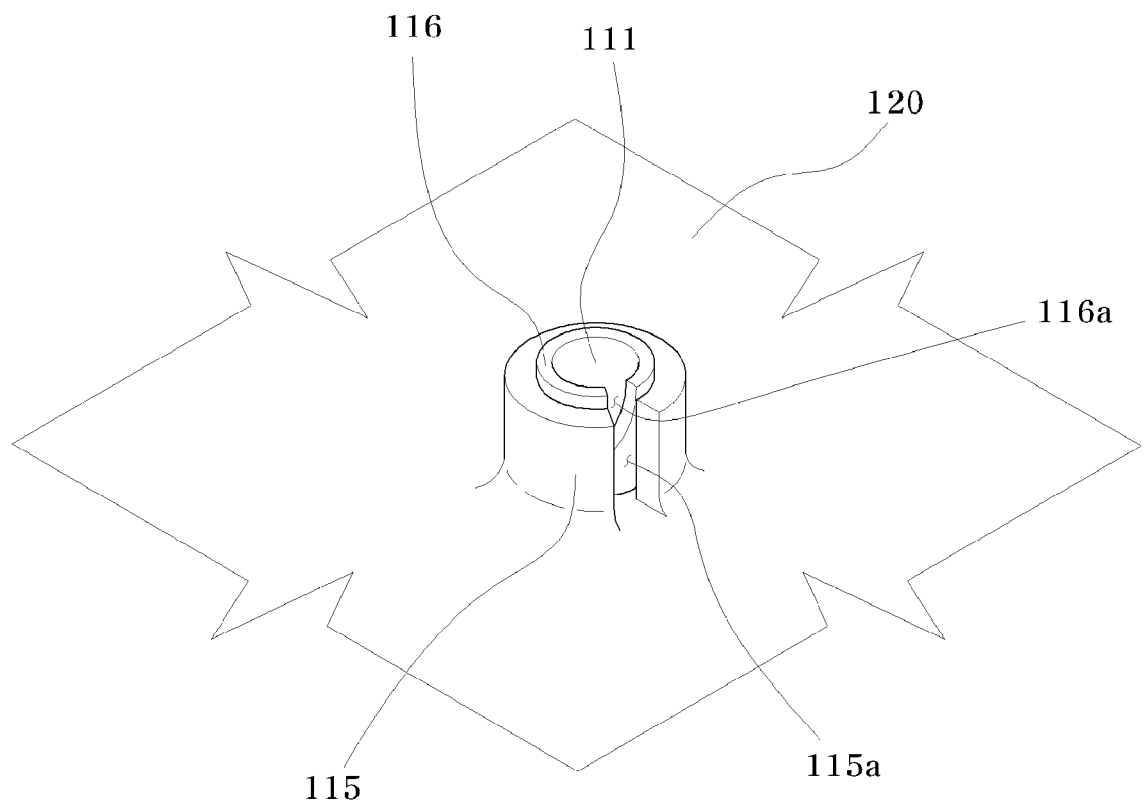
FIG. 33 is a partial perspective view of a water discharge tube and an opening and closing tube, which are provided in a water outlet of a culture bed of DSCAC, which is used for producing potato seedlings according to the present invention.
Figure 34:
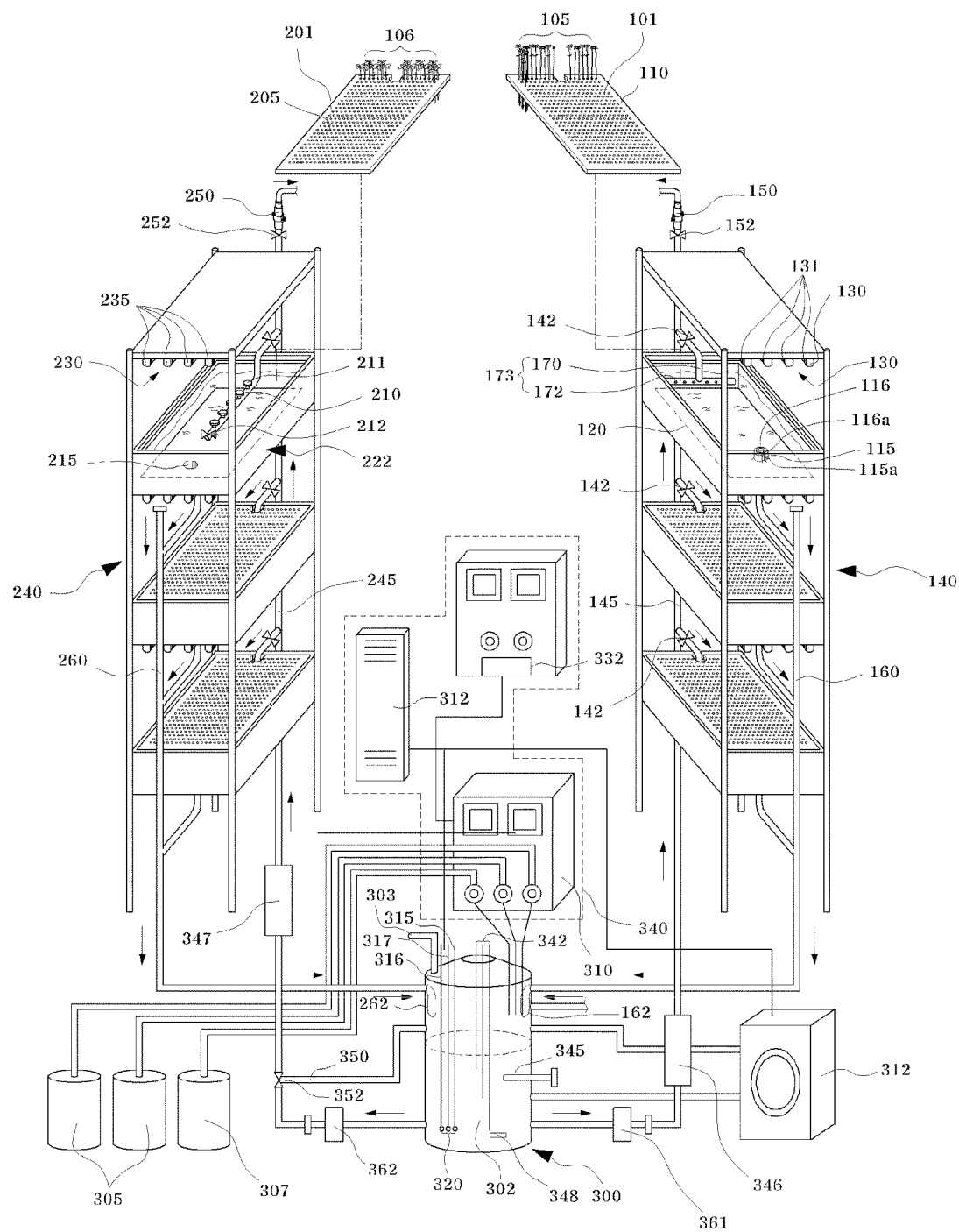
FIG. 34 illustrates the operation of DSCAC and SSCAC, which are used for producing potato seedlings according to the present invention.

FIG. 30 illustrates the construction of DSCAC and SSCAC, which are used for producing potato seedlings according to the present invention. FIG. 31 is a partial perspective view of a culture bed provided in a support frame of DSCAC, which is used for producing potato seedlings according to the present invention. FIG. 32 is a partial perspective view of a culture bed of DSCAC, which is used for producing potato seedlings according to the present invention. FIG. 33 is a partial perspective view of a water discharge tube and an opening and closing tube, which are provided in a water outlet of a culture bed of DSCAC, which is used for producing potato seedlings according to the present invention. FIG. 34 illustrates the operation of DSCAC and SSCAC, which are used for producing potato seedlings according to the present invention.

As illustrated in the drawings, the DSCAC according to the present invention comprises a culture panel 110 in which holes 101 for planting stem cuttings are arranged to plant potato seedlings 105 through stem cutting and cultivate the potato seedlings 105; a culture bed 120 which has a space in which the culture panel 110 is placed, contains a supplied nutrient solution required for the growth of the potato seedlings 105 planted through stem cutting in the culture panel 110, and has a water outlet 111 for discharging excess supplied nutrient solution; a light source 130 which is provided at one side of the culture bed 120 and radiates light onto potato seedlings 105 planted through stem cutting in the culture panel 110; a nutrient solution dispersion and supply tube 173 which is provided at one side of the culture bed 120 and flows and supplies the nutrient solution to the lower part of the culture bed 120; and a nutrient solution preparation and supply part 300 which is equipped with a nutrient solution tank 302, is connected to the nutrient solution dispersion and supply tube 173, and supplies the nutrient solution thereto.

After the potato seedlings 105 have been planted through stem cutting to the culture panel 110, the culture panel 110 is supported by the upper part of the culture bed 120. The roots of the potato seedlings 105 planted in the culture panel 110 through stem cutting grow using nutrients contained in the nutrient solution supplied to the culture bed 120.

The water outlet 111 of the culture bed 120 is provided with a water discharge tube 115 having a slit 115a in a longitudinal direction. An opening and closing tube 116 having a helical opening and closing part 116a is inserted into the water discharge tube 115 in a separated state against a lower part of the water discharge tube 115.

The water discharge tube 115 has a slit 115a through which the nutrient solution contained in the culture bed 120 is discharged. The opening and closing tube 116 controls the water level of the nutrient solution contained in the culture bed 120 according to the length of the opened portion of the slit 115a by controlling the length of the slit 115a, which is connected to the water discharge tube 115, and is opened by rotation.

The opening and closing tube 116 is inserted into the water discharge tube 115 while the slit 115a at the lower part of the water discharge tube 115 is opened, and controls the water level of the nutrient solution according to the length of the opened portion of the slit 115a by rotating an opening and closing part 116a that has a singular structure with the slit 115a, or by rotating the slit 115a to close.

The culture bed 120 is formed in two layers by a support frame 140 in which the space in which the nutrient solution is held is formed in two layers. The nutrient solution dispersion and supply tube 173 connected to the nutrient solution tube 302 is placed in the space formed in each layer of the support frame 140. Fluorescent lamps 131 as the light source are arranged in a double row in a lower part of the culture bed 120 formed in each layer of the support frame 140.

Herein, the nutrient solution dispersion and supply tube 173 in each layer is connected to one side of the support frame 140 to supply the nutrient solution. A main supply tube 145 having a flow control valve 142 for controlling the inflowing amount of the nutrient solution is placed between the nutrient solution dispersion and supply tubes 173. The main supply tube 145 is placed in an upright orientation such that it extends to the upper part of the culture bed 120 placed at the uppermost part of the support frame 140. The uppermost part of the main supply tube 145 is larger in volume than the lower part, and is coupled with a pressure tube 150 connected to the nutrient solution tank 302. A pressure control valve 152 for controlling the pressure of the main supply tube 145 is placed between the main supply tube 145 and the pressure tube 150.

When the main supply tube 145 is fully filled with the nutrient solution supplied thereto, since the main supply tube 145 is in the upright orientation, the main supply tube 145 applies spontaneous pressure to the nutrient solution dispersion and supply tube 173 in proportion to the height of the nutrient solution.

When the main supply tube 145 is overflowing with the nutrient solution, which flows in turn into the pressure tube 150, the nutrient solution has an increased flow rate when it passes through the pressure tube 150, thereby further increasing the pressure against a lower part of the pressure tube 150.

The pressure increase of the main supply tube 145 by the pressure tube 150 is the result of the flow area at the lower part of the pressure tube 150 being narrower than at an upper part thereof. The increased pressure in the main supply tube 145 due to the pressure tube 150 is applied to the nutrient solution dispersion and supply tube 173 connected to the upright main supply tube 145.

That is, the nutrient solution is supplied under a predetermined pressure to the nutrient solution dispersion and supply tube 173 connected to the upright main supply tube 145, flows along the bottom surface of the culture bed 120, and is finally charged into the culture bed 120 to a predetermined height.

The height of the nutrient solution charged into the culture bed 120 is determined according to the extent of opening of the opening and closing tube 116 for the slit 115*a* of the water discharge tube 115. Since the opening and closing tube 116 is coupled with the water discharge tube 115 in a separated state against the lower part of the water discharge tube 115, the lower part of the slit 115*a* of the water discharge tube 115 is open, and the nutrient solution is discharged into the lower part of the slit 115*a* of the opening and closing tube 116.

When the culture panel 110 plated with the potato seedlings 105 through stem cutting is placed in the culture bed 120, the roots of the potato seedlings 105 contact the nutrient solution, thereby being supplied with nutrients, and grow under the light supplied by the light source 130. The light source 130 radiates light on the potato seedlings 105 planted through stem cutting, as follows: a) 0 Lux for 55-65 hours→b) 2,100 Lux for 45-55 hours, 0 Lux for 4-8 hours→c) 3,600 Lux for 35-45 hours, 0 Lux for 4-8 hours→d) 5,500 Lux for 25-35 hours, 0 Lux for 4-8 hours→e) 7,000 Lux for 535-545 hours (lighting for 18-20 hours every day for 30 days), 0 Lux for 120-180 hours (dark condition for 4-6 hours every day for 30 days). The light levels emitted from the light source 130 are controlled by a timer 332.

The water outlet 111 of the culture bed 120 includes a discharge tube 160 which is connected to the nutrient solution tank 302 and transfers the discharged nutrient solution into the nutrient solution tank 302. A micro-sieving net 162 is placed at the terminal end of the discharge tube 160 to filter out sediments or impurities contained in the circulating nutrient solution.

The discharge tube 160 recovers the nutrient solution by transferring it into the nutrient solution tank 302. The micro-sieving net 162 sifts sediments or impurities contained in the nutrient solution recovered after being supplied to the potato seedlings 105, thereby enhancing the purity of the nutrient solution to be supplied again to the culture bed 120.

One side of the nutrient solution dispersion and supply tube 173 is a T-shaped branch tube 170 into which the nutrient solution is supplied from the nutrient solution tank 302. The branch tube 170 has an effusion tube 172 in which nozzles 172*a* from which the nutrient solution flows out are formed, and which is horizontally provided at a lower surface of the culture bed 120. The branch tube 170 is connected to the main supply tube 145 and is supplied with the nutrient solution therefrom. The effusion tube 172 is formed in a transverse direction near the bottom surface of the culture bed 120, and flows, in a longitudinal direction, the nutrient solution supplied from the branch tube 170 to the culture bed 120 through the nozzles 172*a*.

Since the effusion tube 172 is formed in a transverse direction relative to the culture bed 120 and thus evenly flows the nutrient solution in a longitudinal direction, the potato seedlings 105 uniformly grow and their growth is not hindered by the flow pressure of the nutrient solution.

An SSCAC, which is provided at one side of a DSCAC, comprises a culture panel 205 in which holes 201 for planting of stem cuttings are arranged to plant potato seedlings 106 through stem cutting and cultivate them; a culture bed 222 in an upper part of which the culture panel 205 is supported and which has a spray tube 210 having nozzles 211 spraying in a mist form a nutrient solution required for the growth of the potato seedlings 106 planted through stem cutting in the culture panel 205, and a water outlet 215 for discharging the nutrient solution that has been sprayed and has flowed down; a light source 230 which is provided at one side of the culture bed and radiates light on the potato seedlings 106 planted through stem cutting in the culture panel 205; and a nutrient solution preparation and supply part 300 which is equipped with a nutrient solution tank 302, to one side of which the spray tube 210 of the culture bed 222 is connected, and in which the nutrient solution is stored.

The spray tube 210 has a cleaning valve 212 at a terminal part to discharge sediments contained therein when the spray tube 210 is opened. When the nutrient solution in the nutrient solution tank 302 is supplied to the spray tube 210 after the cleaning valve 212 has been opened, the nutrient solution that has flowed out from the nutrient solution tank 302 discharges sediments accumulated inside the spray tube 210.

The culture bed 222 is formed in two layers by a support frame 240 in which the space into which the nutrient solution is sprayed is formed in two layers. The spray tube 210 connected to the nutrient solution tank 302 is placed in the space provided at each layer of the support frame 240, and sprays the nutrient solution from the nutrient solution tank 302 in a mist form.

The spray tube 210 has nozzles 211 for spraying the nutrient solution in a mist form, and is placed at the lower part of the culture bed 222 in a longitudinal direction.

The light source is controlled by a timer 332 to supply the light levels required according to the growth phases of the potato seedlings 106 planted in the culture bed 222 through stem cutting.

The spray tube 210 in each layer is connected to one side of the support frame 240 to supply the nutrient solution. A main supply tube 245 having a flow control valve for controlling the inflowing amount of the nutrient solution is placed between the spray tubes 210. The main supply tube 245 is placed in an upright orientation such that it extends to the upper part of the culture bed 222 placed at the uppermost part of the support frame 240. The uppermost part of the main supply tube 245 has a narrower flow area than the lower part, thereby increasing the pressure in the main supply tube 245 connected to the lower part thereof, and coupled with a pressure tube 250 connected to the nutrient solution tank 302. A pressure control valve 252 is placed at a lower position in the pressure tube 250, and controls the pressure against the main supply tube 245 by controlling the flow levels of the nutrient solution for the pressure tube 250.

Since the pressure tube 250 has a lower flow area than the main supply tube 245, the nutrient solution has an increased flow rate when it passes through the pressure tube 250, and the main supply tube 245 connected to the lower part of the pressure tube 250 maintains higher pressure than the pressure tube 250. This high pressure is applied to the nutrient solution to efflux into the spray tube 210. Since a pressure control valve 252 is formed between the pressure tube 250 and the main supply tube 245 to control the level of flow of the nutrient solution into the pressure tube 250, the pressure of the main supply tube 245 is controlled by controlling the flow levels of the nutrient solution to be recovered in the nutrient solution tank 302 using the pressure control valve 252.

The water outlet 215 of the culture bed 222 includes a discharge tube 260 which is connected to the nutrient solution tank 302 and recovers the discharged nutrient solution into the nutrient solution tank 302. A micro-sieving net 262 is placed at a terminal part of the discharge tube 260 to sift sediments or impurities introduced into the nutrient solution tank 302.

The DSCAC and SSCAC are installed in the same indoor space. In order to cultivate the potato seedlings 105, which are obtained by in vitro culturing growing points collected from a seed potato cultivar that has been ascertained to be virus-free, into potato seedlings 106 suitable for use in hydroponic facilities to obtain seed potatoes, the potato seedlings 105 should be grown to a predetermined length in the culture bed 120 containing the nutrient solution. Then, the potato seedlings 106, which are obtained by cutting an upper part of the potato seedlings 105 to a predetermined length, should be planted through stem cutting in the culture panel 205 of another culture bed 222 in which the nutrient solution is sprayed in a mist form, and grown to a predetermined length.

The DSCAC and SSCAC are provided in such a way that the nutrient solution tank 302 of the nutrient solution preparation and supply part 300 is sandwiched between them, and supplied with the nutrient solution through the operation of nutrient solution supply pumps 361 and 362, which are provided on both sides of the nutrient solution tank 302.

The nutrient solution preparation and supply part 300 comprises a stock solution tub 305 which supplies a stock solution containing organic and inorganic nutrients to prepare the nutrient solution of the nutrient solution tank 302; an acidic solution tub 307 which is provided on one side of the stock solution tub and supplies an acidic solution to the nutrient solution tank 302 to control the acidity of the nutrient solution tank; and a quantization pump 310 which is connected to the stock solution tub 305 and the acidic solution tub 307, and receives the stock solution and the acidic solution and supplies them to the nutrient solution tank 302 in predetermined amounts.

The nutrient solution preparation and supply part 300 further comprises a temperature control part 312 which controls the temperature of the nutrient solution by receiving the nutrient solution, heating it and transferring it to the nutrient solution tank 302; and a sensor part 320 which is equipped with a nutrient solution temperature sensor 315 for measuring the temperature of the nutrient solution stored in the nutrient solution tank 302, a pH sensor 316 for measuring the acidity thereof, and a concentration sensor 317 for measuring the nutrient concentrations of the nutrient solution.

The nutrient solution preparation and supply part 300 further comprises a control part 340 which controls the temperature of the nutrient solution by measuring the temperature of the nutrient solution using the nutrient solution temperature sensor 315 and operating the temperature control part 312, and controls the amount of the stock solution and the acidic solution supplied to the nutrient solution tank 302 through the quantization pump 310 by checking the temperature, concentration and acidity of the nutrient solution using the pH sensor 316 and the concentration sensor 317.

The nutrient solution preparation and supply part 300 includes a water level sensor 342 which senses the water level of the nutrient solution tank 302. The nutrient solution tank 302 of the nutrient solution preparation and supply part 300 is equipped with a water disinfection part 345 which disinfects the nutrient solution, and a bubble generation part 348 which generates bubbles in the nutrient solution.

Ultraviolet disinfection parts 346 and 347 are placed in a tube connecting the nutrient solution tank 302 and the culture beds 120 and 222 in order to disinfect the nutrient solution.

Referring to FIG. 34, a process for supplying the nutrient solution prepared by the nutrient solution preparation and supply part 300 to the potato seedlings 105 and 106 of the culture beds 120 and 222 will be described below.

First, when the quantization pump 310 is operated, the stock nutrient solution in the stock solution tub 305 and the acidic solution in the acidic solution tub 307 are supplied to the nutrient solution tank 302, and raw water is supplied to the nutrient solution tank 302 through a raw water tube 303.

The control part 340 senses the acidity and concentration of the nutrient solution through the pH sensor 316 and the concentration sensor 317 provided in the nutrient solution tank 302, and controls the quantization pump 310 in order to control the amount of the stock solution and the acidic solution, which are supplied through the quantization pump 310, thereby adjusting the acidity and concentration of the nutrient solution prepared in the nutrient solution tank 302 to levels appropriate for the growth of the potato seedlings 105 and 106.

The control part 340 senses the temperature of the nutrient solution using the temperature sensor 315 provided in the nutrient solution tank 302, and circulates the nutrient solution into the temperature control part 312, thereby adjusting the temperature of the nutrient solution to the temperature required for the growth of the potato seedlings 105 and 106.

The nutrient solution is disinfected by operating the water disinfection part 345 provided inside the nutrient solution tank 302. The bubble generation part 348 generates bubbles to supply oxygen to the nutrient solution.

When the nutrient solution supply pump 361 provided in a lateral part of the nutrient solution tank 302 is operated, the nutrient solution is supplied to the culture bed 120 provided in the nutrient solution dispersion and supply tube 173. The nutrient solution is disinfected with ultraviolet radiation once more when it passes through the ultraviolet disinfection part 346 provided in the lower part of the main supply tube 145.

The main supply tube 145 is filled with the supplied nutrient solution. When the main supply tube 145 is filled with the nutrient solution up to the pressure tube 150 provided at an upper part thereof, the flow control valve 142 between the nutrient solution dispersion and supply tube 173 and the main supply tube 145 is opened in order to supply the nutrient solution to the branch tube 170 of the nutrient solution dispersion and supply tube 173 and flow the nutrient solution to the lower part of the culture bed 120 through the effusion tube 172 of the branch tube 170.

The nutrient solution is contained in the culture bed 120 up to a predetermined water level. Nutrient solution above the predetermined water level is recovered to the nutrient solution tank 302 through the slit 115a of the water discharge tube 115, which is provided in the water outlet 111 of the culture bed 120.

That is, the length to which the slit 115a of the water discharge tube 115 is opened is controlled by the opening and closing tube 116. The nutrient solution effluxes through a predetermined part of the opened slit 115a. The opening and closing part 116a provided in the opening and closing tube 116 is formed in a helical form to allow the slow influx of the nutrient solution from a lateral direction, thereby preventing the roots of the potato seedlings 105 planted in the culture panel 110 through stem cutting from being affected by the flow of the discharged nutrient solution.

The slit 115a at the lower part of the water discharge tube 115 is always opened because the opening and closing tube 116 is inserted into the water discharge tube 115 in a separated state against the lower part of the water discharge tube 115. When the operation of the nutrient solution supply pump 361 is stopped to interrupt the supply of the nutrient solution from the nutrient solution dispersion and supply tube 173, the nutrient solution is discharged through the lower opening of the slit 115a.

When the supply of the nutrient solution from the nutrient solution dispersion and supply tube 173 is interrupted, the nutrient solution is discharged, and thus, the supply of the nutrient solution to the roots of the potato seedlings 105 is interrupted. The roots of the potato seedlings 105 are dried in the air, thereby preventing root rot or stem soft rot, which usually occurs when the nutrient solution is continuously contained in the culture bed 120.

The nutrient solution discharged through the water outlet 111 of the culture bed 120 flows again into the nutrient solution tank 302 through the discharge tube 160. The microsieving net provided at the terminal end of the discharge tube 160 filters out sediments or impurities contained in the nutrient solution, thereby preventing the re-supplied nutrient solution from being contaminated with the sediments or impurities.

When the nutrient solution in the nutrient solution tank 302 is supplied to the culture bed 120, the light source 130 is operated to radiate light onto the potato seedlings planted in the culture panel 110 through stem cutting, as follows: a) 0 Lux for 55-65 hours→b) 2,100 Lux for 45-55 hours, 0 Lux for 4-8 hours→c) 3,600 Lux for 35-45 hours, 0 Lux for 4-8 hours→d) 5,500 Lux for 25-35 hours, 0 Lux for 4-8 hours→e) 7,000 Lux for 535-545 hours (lighting for 18-20 hours every day for 30 days), 0 Lux for 120-180 hours (dark condition for 4-6 hours every day for 30 days).

The light source 130 includes four fluorescent lamps placed in the lower part of the culture bed 120. The time for which light is supplied by the fluorescent lamps 131 is controlled by a timer 332. The timer 332 controls light levels by regulating the number of illuminated fluorescent lamps 131 and the time that each fluorescent lamp is illuminated.

When the potato seedlings 105 grow to a predetermined length in the culture bed 120, workers cut the potato seedlings 105 to a predetermined length. The stem cuttings are planted and grown in the culture bed 222 provided at the opposite side of the nutrient solution tank 302. This ensures multiple node formation and stem hardness in the roots of the potato seedlings 105, thereby growing the potato seedlings into potato seedlings suitable for producing seed potatoes in hydroponic facilities.

That is, the stem cuttings of the potato seedlings 106 from the culture bed 120 provided on the right side of the nutrient solution tank 302 are planted in the culture panel 205 of the culture bed 222 provided on the left side of the nutrient solution tank 302. When the nutrient solution supply pump 362 provided on the left side of the nutrient solution tank 302 is operated, the nutrient solution is disinfected through the ultraviolet disinfection part 347 provided at the main supply tube 245, and supplied to the spray tube 210 provided over the culture bed 222. The nozzles formed in a row in the spray tube 210 spray the nutrient solution in a mist form. The sprayed nutrient solution bounces off of both inner wall surfaces of the culture bed 222 and is then sprayed, thereby being supplied to the root zone of the potato seedlings 106.

After the nutrient solution is supplied to the potato seedlings, it flows down to the lower part of the culture bed 222, and is recovered in the nutrient solution tank 302 through the water outlet 215. The discharge tube 260 recovering the nutrient solution has the micro-sieving net 262 at a terminal part thereof in order to sift sediments and impurities from the recovered nutrient solution.

When the light source 230 provided at the lower part of the culture bed 222 is turned on, the fluorescent lamps 235 comprising the light source 230 are operated. The fluorescent lamps 235 are controlled by the timer 332, thus the potato seedlings 106 grow into potato seedlings suitable for planting in hydroponic facilities.

In addition, the present invention provides a method of mass producing seed potatoes, comprising planting the potato seedlings produced according to the above method in hydroponic facilities; maximizing the number of stolons by carrying out stem descending work for the planted potato seedlings two or three times; and harvesting potato minitubers formed at the stolons. For the mass production of seed potatoes, the potato seedlings planted in hydroponic facilities preferably have a length of 30-40 cm. The inside of hydroponic facilities is preferably maintained at 18-21° C. The light levels, which are measured during the day time from twelve to one o'clock, are preferably 80,000-100,000 Lux on clear days, 25,000-35,000 Lux on cloudy days, and 10,000 Lux on rainy days. The nutrient solution used has a pH value from 6.6 to 7.0. Preferably, the nutrient solution is supplied for 30 sec, and supply thereof is then interrupted for 4 min.

A better understanding of the present invention may be obtained through the following examples which are set forth to illustrate, but are not to be construed as the limit of the present invention.

EXAMPLE 1

Production of Potato Seedlings

1. Collection of Growing Points from Seed Potatoes and Liquid Culture

Disease-free seed potatoes were selected from a known potato cultivar. They were grown under semi-shaded diffused light until potato eyes (sprouts) thereof were about 0.5 cm, or were potted in sterile perlite about two times as deep as the size of the potatoes. Herein, the seed potatoes were isolated from contaminants, including insect vectors such as mites, using a 540 mesh.

One node at an upper part of the stem of the illuminated seed potatoes, which has growing points of eyes or sprouts, was treated with one or two drops of Tween-20 as a surfactant, sufficiently rinsed with running water, placed into a container having a lid, and transferred to a clean bench.

The rinsed node was surface-disinfected with 70-75% ethanol for 30 sec, and rinsed with sterile water two or three times. The node was surface-disinfected with 2% hypochlorite for 5-10 min, and rinsed with sterile water two or three times. After the node was transferred to a schale, a growing point was collected in a size of 0.2-0.3 mm (having about two primordial leaves) under a microscope. The collected growing points were planted in a liquid medium of pH 5.8, which was prepared with an MS basic medium and 30 g/L sucrose, and incubated for 25 days in a rotary shaker at 80 rpm.

2. Pathogen Testing for In Vitro Tissue-cultured Plantlets Using ELISA

Since a large number of individuals should be obtained for pathogen testing of in vitro plantlets grown in the liquid medium, the in vitro plantlets were propagated about four times in 500-ml culture bottles containing 200 ml of a solid medium.

After each plantlet was labeled for identification, a test sample was collected. Juices were extracted from eighteen subcultured seedlings in the same parental line. An antibody was diluted 1,000 times with a standard coating buffer (20 µl antibody in 20 ml buffer), and 200 µl of the antibody dilution were added to each well of a 96-well plate. The 96-well plate was incubated in a humid container at 30° C. for 4 hrs. The 96-well plate was then washed with washing buffer four to eight times, and all of the water was removed from the plate. Each juice was diluted to a 1:10 or 1:20 ratio with extraction buffer, and 200 μl of this dilution was added to each well. The 96-well plate was incubated in the humid container at 4° C. for 16 hrs (overnight). The 96-well plate was washed with washing buffer four to eight times, and water was completely removed from the plate. Conjugate IgG was diluted to 1,000 times with conjugate buffer, and 200 μl of this dilution was added to each well. The 96-well plate was incubated in the humid container at 30° C. for 5 hrs. The 96-well plate was then washed with washing buffer four to eight times. One substrate pill was dissolved in 20 ml of substrate buffer, and 200 μl of this dilution was added to each well. The 96-well plate was incubated under a dark condition at room temperature for 1 hr. Absorbance was measured at 405 nm using a microplate reader (Bio-Rad, Model 550).

3. Subculture and Propagation of Pathogen-tested In Vitro Plantlets

The pathogen-tested in vitro plantlets were planted in 500-ml culture bottles containing 200 ml of a solid medium, which was prepared with a basic MS medium of pH 5.8 supplemented with 70-80 g/L of sucrose and 9 g/L of agar. The plantlets were then allowed to grow in a culture room under 4,500 Lux lighting for 18-20 hrs, and 0 Lux for 4-6 hrs for 30 days, the room temperature being maintained at 21° C. using an air conditioner.

Then, the plantlets were planted in 500-ml culture bottles containing 200 ml of a solid medium, which was prepared with a basic MS medium having a pH of 5.8 supplemented with 9 g/L of agar, 80 g/L of sucrose and 0.025 mg/L of coumarin. The plantlets were incubated until the leaves had fallen off and only stems remained, in a culture room under 4,500 Lux lighting for 18-20 hrs, and 0 Lux for 4-6 hrs using 4D fluorescent lamps, wherein the room temperature was maintained at 21° C. using an air conditioner.

4. DSCA of Potato Seedlings

The propagated potato seedlings were planted through stem cutting and cultivated in a DSCAC, which was prepared using a square aluminum tube having a size of 4 cm. The DSCAC had a three layer structure of 132 cm long×60 cm wide×230 cm high, in which each layer was 45 cm high.

After the potato seedlings were removed from the culture bottles, node regions at lower parts of stems were cut out using a disinfected sharp knife. The cuttings were planted in holes for planting stem cuttings in DSCAC. The indoor temperature was maintained at 18° C. The radiation started from 0 Lux for 60 hrs, and the light intensity was gradually increased to 2,100 Lux for 45-55 hours, 0 Lux for 4-8 hours→3,600 Lux for 35-45 hours, 0 Lux for 4-8 hours→5,500 Lux for 25-35 hours, 0 Lux for 4-8 hours→7,000 Lux for 535-545 hours (lighting for 18-20 hours every day for 30 days), 0 Lux for 120-180 hours (dark condition for 4-6 hours every day for 30 days), thereby hardening the stem cuttings. A nutrient solution having a pH of 6.8 was used. The nutrient solution was supplied for 30 min, and the supply thereof was interrupted for 120 min. Potato seedlings were repeatedly collected 13-15 days after planting of stem cuttings at time intervals of 6-10 days until nodes were exhausted.

5. SSCA of Potato Seedlings

The potato seedlings, having undergone deep-flow-stem-cutting-and-acclimatization, were planted through stem cutting in a SSCAC, which was prepared using a square aluminum tube having a size of 4 cm. The SSCAC had a three layer structure 260 cm long×60 cm wide×230 cm high, in which each layer was 60 cm high. The SSCA was carried out using a nutrient solution of pH 6.8 under 7,000 Lux lighting for 18-20 hrs, and 0 Lux for 4-6 hrs at 21° C. The nutrient solution was supplied to the potato seedlings in the form of microparticles (mist particles) through spray nozzles. The nutrient solution sprayed onto the potato seedlings was supplied for 30 sec, and the supply of the nutrient solution was interrupted for 4 min. The supply and interruption thereof of the nutrient solution were repeatedly alternated. When the above-ground portion of potato seedlings had grown to about 10 cm in length, lower leaves, other than the three uppermost leaves, were removed with disinfected scissors, and stem descending work was carried out three times by descending the stems of potato seedlings below the culture panel. All of the lower leaves, but not the three uppermost leaves, were removed during the last 5-7 days of SSCA. The roots of potato seedlings were cut to remove three quarters thereof, and then allowed to regenerate.

EXAMPLE 2

Production of Seed Potatoes

The potato seedlings having a plant length of 35 cm, prepared in Example 1, were planted in hydroponic facilities. The potato seedlings were cultivated at 21° C. using a nutrient solution of pH 6.8. The nutrient solution sprayed onto the potato seedlings was supplied for 30 sec, and the supply of the nutrient solution was interrupted for 4 min. The supply and interruption thereof of the nutrient solution were repeatedly alternated. When the above-ground portion of the potato seedlings had grown to about 10 cm in length, the lower leaves, but not the three uppermost leaves, were removed with disinfected scissors, and stem descending work was carried out three times by descending the stems of potato seedlings below the culture panel. Thereafter, potato minitubers were repeatedly collected.

TEST EXAMPLES 1 to 3

In order to determine conditions suitable for planting through stem cutting and acclimatizing tissue-cultured plantlets in DSCAC, the in vitro potato seedlings were evaluated for seedling quality and survival rates upon stem-cutting and acclimation according to the amount of supplemented components of MS medium.

The culture seedlings obtained from growing points collected from a seed potato cultivar, were tested for infection with viruses (PLRV, PVY, PVX, PVM, PVS and AMV) for selection of disease-free individuals. Then, plantlets were planted in 500-ml culture bottles containing 200 ml of a solid medium, which was prepared with a basic MS medium of pH 5.8 supplemented with 9 g/L of agar, and incubated for 25 days in a culture room under 4,500 Lux lighting for 18-20 hrs, and 0 Lux for 4-6 hrs using 4D fluorescent lamps, wherein the room temperature was maintained at 21° C. using an air conditioner. The in vitro potato seedlings were examined for growth states and survival rates upon stem-cutting and acclimation according to the amount of supplemented components of the medium. A known potato cultivar, "Superior", was used in this test.

The results are given in Tables 1 to 3, below.

TABLE 1

| | Sucrose (g/L) | | | | | | | |
|---|---|---|---|---|---|---|---|---|
| | 0 | 20 | 40 | 60 | 80 | 100 | 120 | 140 |
| Plant length (cm/plant) | 5.0 | 6.2 | 7.4 | 9.3 | 9.5 | 6.1 | 5.2 | 2.1 |
| Fresh weight (cm/plant) | 0.45 | 0.47 | 0.53 | 0.58 | 0.75 | 0.69 | 0.63 | 0.67 |
| Survival rates of stem cuttings | 13% | 27% | 34% | 59% | 71% | 68% | 67% | 72% |

Table 1 shows the seedling quality and survival rates of the in vitro tissue-cultured plantlets according to the amount of sucrose added to the MS medium as an energy source. As shown in Table 1, sucrose was most beneficial to the in vitro plantlets when used in an amount of 80 g/L, as indicated by plant length, fresh weight and survival rates of stem cuttings.

TABLE 2

| | Coumarin (mg/L) | | | | | | | | | | | | | |
|---|---|---|---|---|---|---|---|---|---|---|---|---|---|---|
| | 0 | | 0.010 | | 0.015 | | 0.020 | | 0.025 | | 0.030 | | 0.035 | |
| | Sucrose (g/L) | | | | | | | | | | | | | |
| | 30 | 80 | 30 | 80 | 30 | 80 | 30 | 80 | 30 | 80 | 30 | 80 | 30 | 80 |
| Plant length (cm/plant) | 5.3 | 8.6 | 6.1 | 7.8 | 6.5 | 7.9 | 6.7 | 8.1 | 6.9 | 9.5 | 6.7 | 8.3 | 6.4 | 8.2 |
| Fresh weight (cm/plant) | 0.53 | 0.72 | 0.57 | 1.12 | 0.63 | 1.13 | 0.71 | 1.31 | 0.84 | 1.65 | 0.86 | 1.39 | 0.71 | 1.36 |
| Survival rates of stem cuttings | 33 | 70 | 73 | 90 | 78 | 92 | 80 | 100 | 83 | 100 | 88 | 100 | 81 | 100 |

Table 2 shows the seedling quality and survival rates of the in vitro tissue-cultured plantlets according to the amount of sucrose and coumarin added to the MS medium. As shown in Table 2, when the MS medium was supplemented with 80 g/L of sucrose and 0.025 mg/L of coumarin, the highest seedling quality and survival rates were obtained.

TABLE 3

| | Hyponex (g/L) | | | | | | | |
|---|---|---|---|---|---|---|---|---|
| | 0 | | 1 | | 2 | | 3 | |
| | Sucrose (g/L) | | | | | | | |
| | 30 | 80 | 30 | 80 | 30 | 80 | 30 | 80 |
| Plant length (cm/plant) | 7.2 | 7.59 | 6.2 | 8.1 | 5.4 | 7.98 | 5.6 | 7.82 |
| Fresh weight (cm/plant) | 0.53 | 1.03 | 0.61 | 1.19 | 0.56 | 1.08 | 0.57 | 1.01 |
| Survival rates of stem cuttings | 28 | 79 | 69 | 83 | 55 | 80 | 57 | 77 |

Table 3 shows the seedling quality and survival rates of the in vitro tissue-cultured plantlets according to the amount of sucrose and hyponex added to the MS medium. As shown in Table 3, the use of hyponex resulted in lower seedling quality and survival rates than when coumarin was used.

The results of Test Examples 3 indicate that the basic medium supplemented with 80 g/L of sucrose and 0.025 mg/L of coumarin is suitable for producing high quality potato seedlings.

TEST EXAMPLE 4

This test was performed to establish an effective method for producing potato seedlings according to the acclimatization of in vitro tissue-cultured plantlets. The pathogen-tested seedlings were allowed to grow for 30 days in a solid medium, which was prepared from a basic MS medium at a pH of 5.8 supplemented with 9 g/L of agar and 30 g/L of sucrose, and a liquid medium, which was prepared like the solid medium but excluding agar, in a culture room at 21° C. under 4,500 Lux lighting for 18-20 hrs, and 0 Lux for 4-6 hrs using 4D fluorescent lamps.

In Group A, the in vitro plantlets were removed from culture bottles and immediately planted through stem cutting without general acclimatization. In contrast, Group B was subjected to an acclimatization process after being cultured in vitro. That is, the in vitro plantlets were placed in a greenhouse having the same light intensity and other conditions as in the culture room. The light intensity in the greenhouse was gradually increased at time intervals of two to three days. Three to four days before being planted in facilities, aluminum foil was removed from culture bottles to allow the in vitro plantlets to adapt to atmospheric humidity. Then, the in vitro plantlets were removed from the culture bottles, and cut at node regions at lower parts of stems using a disinfected sharp knife. Each test group consisted of 500 individuals, and a known potato cultivar "Superior" was used in this test.

For perlite culture, three or four nodes containing growing points were cut from the in vitro-cultured disease-free seedlings with a disinfected sharp knife, and directly planted in a sterile perlite-containing box for raising seedlings on a small scale. In an alternative method, the plantlets were planted in the perlite box in a way such that their roots developed upon in vitro culture. Sufficient 1:2 diluted MS solution was supplied at time intervals of three days in order to prevent the plantlets from drying.

For deep culture, a culture bed of a deep flowing culture system was completely filled with a nutrient solution, and oxygen was supplied to the nutrient culture using an air pump. For deep flow culture, a nutrient solution supplied through a water outlet of a culture bed continuously flowed while contacting the roots of seedlings.

For DSCAC, a nutrient solution supplied to a culture bed was completely drained and discharged through a helical discharge unit for water level control, which was placed below the nutrient solution, thereby completely exposing the roots of potato seedlings in the discharged culture bed to the air and enabling air influx and circulation through holes for planting stem cuttings in an upper board of the culture bed. The nutrient solution was supplied for 30 min to the culture bed, and the supply of the nutrient solution was interrupted for 90 min. The supply and interruption thereof of the nutrient solution were alternatively performed.

The results are given in Table 4, below.

TABLE 4

|  | Perlite | | Deep culture | | Deep flow culture | | DSCAC | |
|---|---|---|---|---|---|---|---|---|
| Test group | A | B | A | B | A | B | A | B |
| Death due to desiccation/# of plants | 127 | 103 | 132 | 106 | 102 | 97 | 84 | 99 |
| Soft rot/# of plants | 291 | 181 | 267 | 160 | 211 | 134 | 37 | 29 |
| Acclimatized and survived individual number/# of plants | 82 | 216 | 101 | 234 | 187 | 269 | 379 | 372 |

As shown in Table 4, the in vitro-cultured seedlings cultivated in the DSCAC according to the present invention had the lowest death rates due to desiccation, the lowest soft rot occurrence and the highest numbers of acclimatized and survived individuals. These results indicate that the DSCAC is the most effective method for acclimatizing in vitro-culture plantlets.

TEST EXAMPLE 5

In order to investigate the occurrence of soft rot according to the discharged state of the nutrient solution supplied to the root zone of stem cuttings of in vitro-cultured potato seedlings, the in vitro-cultured plantlets produced according to the same method as in Test Example 4 were tested under various conditions described in Table 5, below.

TABLE 5

| | Nutrient solution level (discharged state) | | | |
|---|---|---|---|---|
| | Nutrient solution circulation (supplied for 24 hrs) | ½ discharge (below the root zone) | 1/10 discharge (remaining in the bottom) | Complete discharge |
| Soft rot occurrence/plant | 500 | 455 | 189 | 41 |

TABLE 5-continued

| | Nutrient solution level (discharged state) | | | |
|---|---|---|---|---|
| | Nutrient solution circulation (supplied for 24 hrs) | ½ discharge (below the root zone) | 1/10 discharge (remaining in the bottom) | Complete discharge |
| Acclimatized and survived individual number/plant | 0 | 5 | 311 | 459 |

As shown in Table 5, good ventilation through complete discharge at the root zone of potato seedlings planted through stem cutting prevents softening of cut regions, as well as preventing root rot due to excessive water supply.

TEST EXAMPLE 6

In order to determine a suitable time for supplying nutrient solution to the potato seedlings planted through stem cutting, in vitro-culture plantlets having a size of 6 cm, which were produced according to the same method as in Test Example 4, were tested at an indoor temperature of 21° C. and 4,500 Lux for 18-20 hrs, and 0 Lux for 4-6 hrs under various conditions described in Table 6, below.

TABLE 6

| | Nutrient solution supply interruption/supply | | | | | | |
|---|---|---|---|---|---|---|---|
| | 30 min/ 30 min | 60 min/ 30 min | 90 min/ 30 min | 120 min/ 30 min | 160 min/ 30 min | 180 min/ 30 min | 210 min/ 30 min |
| Plant length (cm/plant) | 16.9 | 16.2 | 15.0 | 14.7 | 14.4 | 13.3 | 12.2 |
| Damage due to desiccation/# of plants | 70 | 74 | 81 | 82 | 87 | 106 | 113 |
| Damage due to soft rot/# of plants | 31 | 27 | 13 | 5 | 3 | 2 | 2 |

As shown in Table 6, the frequent supply of the nutrient solution was beneficial to the growth of potato seedlings, but caused soft rot due to excessive water absorption. A long interruption of the nutrient solution supply caused wilting due to water evaporation from the plantlets, resulting in damage due to desiccation. When the nutrient solution was supplied for 30 min, and this supply was then interrupted for 120 min, the amount of damage due to desiccation and soft rot decreased.

TEST EXAMPLES 7 and 8

In order to investigate the effects of flow rates and circulation of a nutrient solution supplied to a culture bed on the rooting of the potato seedlings planted through stem cutting, in vitro-culture plantlets having a size of 6 cm, which were produced according to the same method as in Test Example 4, were planted through stem cutting in DSCAC according to the present invention, and cultivated using a nutrient solution, which was supplied for 30 min and interrupted for intervals of 120 min, at an indoor temperature of 21° C. under 4,500 Lux lighting for 18-20 hrs, and 0 Lux for 4-6 hrs. The radiation was performed two times per day at 8:00 am and 8:00 pm.

TABLE 7

|  | Straight-shaped supply tube (0.5 × 5 cm) | | Circular supply tube (2.5 cm diameter) | | Water pressure dispersion and supply tube (T) |
|---|---|---|---|---|---|
|  | One-nozzle | Three-nozzle | One-nozzle | Three-nozzle |  |
| Rooting day/100 plants | 6.0 | 5.5 | 6.5 | 5.5 | 4.5 |
| Root length on about Day 10 after planting (cm/100 plants) | 0.5 | 1.1 | 0.7 | 1.0 | 1.8 |

TABLE 8

| | Distance from supply tube for supplied nutrient solution (2.5 cm diameter, 1 hp pump) | | | | | | |
|---|---|---|---|---|---|---|---|
|  | Nutrient solution-inflow point | 20 cm | 40 cm | 60 cm | 80 cm | 100 cm | 120 cm |
| First rooting day/30 plants | 4.5 | 4.0 | 3.5 | 3.5 | 3.0 | 3.0 | 3.0 |
| Root length on about Day 10 after planting (cm/100 plants) | 0.4 | 0.7 | 1.5 | 1.7 | 1.9 | 1.9 | 1.9 |

As shown in Tables 7 and 8, the rapid flow rate and swirling due to water pressure generated by the supplied nutrient solution stress the potato seedlings planted through stem cutting, thereby inhibiting the growth and rooting thereof.

TEST EXAMPLE 9

This test was performed to determine an effective method for shoot generation through radiation, among the acclimatization conditions of in vitro plantlets planted through stem cutting in DSCAC.

A known potato cultivar, "Superior", was cultivated through in vitro culture in a solid medium, which was prepared with a basic MS medium having a pH of 5.8 supplemented with 9 g/L of agar, 80 g/L of sucrose and 0.025 mg/L of coumarin, under 4,500 Lux lighting for 18-20 hrs, and 0 Lux for 4-6 hrs. 500 individuals of the in vitro tissue-cultured Superior were cut with a disinfected sharp knife to a length of about 6 cm containing growing points. Cuttings were arranged in a randomized complete block design with three replications. The cuttings were grown with a nutrient solution, which was supplied for 30 min at an interruption interval of 120 min, at room temperature of 21° C. under light levels of 0 Lux, 2,100 Lux, 3,600 Lux and 5,500 Lux using 40D fluorescent lamps. The length of potato seedlings was calculated by taking the mean length of entire normally growing stem cuttings. The internode length was calculated by dividing the measured plant length by the mean number of stem nodes.

TABLE 9

| | Radiation | | | | | | | | | |
|---|---|---|---|---|---|---|---|---|---|---|
| | 0 Lux (dark condition) | | | | | 2,100 Lux | | | | |
| | Treatment period (day) | | | | | | | | | |
| | 0 | 1 | 2 | 3 | 4 | 0 | 1 | 2 | 3 | 4 |
| Plant length (cm/plant) | 6.3 | 6.7 | 9.4 | 11.9 | 13.1 | 6.0 | 6.1 | 6.7 | 7.8 | 9.3 |
| Internode length (cm/plant) | 0.8 | 0.9 | 1.2 | 1.5 | 2.0 | 0.8 | 0.8 | 0.9 | 1.0 | 1.2 |
| Shoot generation (%) | 0 | 38 | 82 | 100 | 100 | 0 | 13 | 35 | 59 | 75 |
| Damage due to soft/# of plants | 0 | 0 | 0 | 3 | 77 | 0 | 0 | 0 | 5 | 9 |
| Damage due to desiccation/# of plants | 0 | 0 | 0 | 0 | 2 | 0 | 8 | 15 | 29 | 11 |
| | 3,600 Lux | | | | | 5,500 Lux | | | | |
| | Treatment period (day) | | | | | | | | | |
| | 0 | 1 | 2 | 3 | 4 | 0 | 1 | 2 | 3 | 4 |
| Plant length (cm/plant) | 6.3 | 6.4 | 6.6 | 7.2 | 8.1 | 6.3 | 6.3 | 6.5 | 7.1 | 7.9 |
| Internode length (cm/plant) | 0.8 | 0.8 | 0.8 | 0.9 | 1.0 | 0.8 | 0.8 | 0.8 | 0.9 | 1.0 |
| Shoot generation (%) | 0 | 11 | 22 | 32 | 55 | 0 | 10 | 23 | 34 | 59 |
| Damage due to soft/# of plants | 0 | 0 | 0 | 4 | 12 | 0 | 0 | 0 | 1 | 18 |
| Damage due to desiccation/# of plants | 0 | 3 | 16 | 29 | 2 | 0 | 7 | 29 | 36 | 1 |

As shown in Table 9, compared to the acclimatization process of adapting in vitro plantlets to the external environment in order to produce potato seedlings using the in vitro plantlets, which depends on the experience and skill of growers, it was more cost-effective to place potato seedlings planted through stem cuttings in dark conditions for a period of two to three days and then slowly harden the shoot sprouts generated at terminal and lateral buds of the planted stem cuttings to use the stem cuttings as potato seedlings.

TEST EXAMPLE 10

This test was performed in order to determine light levels and radiation time suitable for the hardness of shoot sprouts generated after the in vitro-cultured plantlets planted through stem cutting in DSCAC were incubated under dark conditions.

The known potato cultivar "Superior" was cultivated through in vitro culture using a solid medium, which was prepared with a basic MS medium of pH 5.8 supplemented with 9 g/L of agar and 80 g/L of sucrose, under 4,500 Lux lighting for 18-20 hrs, and 0 Lux for 4-6 hrs. 500 individuals of the in vitro tissue-cultured Superior were cut with a disinfected sharp knife to a length of about 6 cm containing growing points. The plantlets were then planted and grown at room temperature, 21° C., using a nutrient solution, which was supplied for 30 min and interrupted for intervals of 120 min. The light intensity was gradually increased using a timer, and the light was radiated on the planted stem cuttings.

Table 10 shows the states of the in vitro-cultured plantlets grown for 15 days after being planted through stem cutting. In Table 10, the controlled radiation time (day) is expressed, for example, as 3→1→1→1→9, which represents 3 days (the first step/0 Lux)→1 day (the second step/2,100 Lux)→1 day (the third step/3,600 Lux)→1 day (the fourth step/5,500 Lux)→9 days (the fifth step/7,000 Lux).

TABLE 10

| | Controlled radiation time | | | |
| --- | --- | --- | --- | --- |
| | 3→1→1→1→9 | 3→2→2→2→6 | 3→3→3→3→3 | 3→2→1→1→8 |
| Plant length (cm/plant) | 10.4 | 13.1 | 16.1 | 12.8 |
| Internode length (cm/plant) | 1.1 | 1.1 | 1.5 | 1.1 |
| Node No./# of plants | 9.6 | 12.3 | 10.8 | 11.7 |
| Fresh weight (g/plant) | 0.27 | 0.28 | 0.29 | 0.29 |
| Damage due to desiccation/# of plants | 62 | 19 | 4 | 13 |
| Damage due to soft/# of plants | 6 | 12 | 58 | 18 |

As shown in Table 10, rapidly increased light levels acted as stressors on the sprouts from terminal and lateral buds generated from the in vitro-cultured plantlets under the dark conditions, the sprouts having low adaptability to light. Radiation with suitable light levels on the generated sprouts may produce potato seedlings having stems with many robust and healthy nodes, which are required in hydroponics.

TEST EXAMPLE 11

This test was performed in order to establish automated controlled radiation according to the acclimatization of potato seedlings planted through stem cutting and the hardening degree of stems based on the results of Test Example 10. The potato seedlings were grown at room temperature of 21° C. using a nutrient solution, which was supplied for 30 min at an interruption interval of 120 min.

TABLE 11

| | The quality of potato seedlings (grown for 30 days) | | | | |
| --- | --- | --- | --- | --- | --- |
| Automated control of radiation time | Plant length (cm/plant) | Internode length (cm/plant) | Fresh weight (g/plant) | Damage due to desiccation/plant | Damage due to soft/plant |
| Planting through stem cutting →60 h/0 Lux→ 50 h/2,100 Lux→ 40 h/3,600 Lux→ 30 h/5,500 Lux→ 540 h/7,000 Lux | 17.7 | 1.1 | 16.1 | 0 | 0 |

As apparent from the data of Table 11, when only disease-free tissue-cultured seedlings are selected and planted through stem cutting by improving the unstable survivability of in vitro-cultured plantlets through rapid shoot generation and suitably increasing the light intensity to the levels required for acclimatization, anyone may stably produce potato seedlings for use in planting in hydroponic facilities.

TEST EXAMPLE 12

This test was performed in order to investigate the collection amount of potato seedlings for cutting according to the growth of potato seedlings planted through stem cutting under automated controlled radiation. The potato seedlings were grown at room temperature, 21° C., using a nutrient solution, which was supplied for 30 min at an interruption interval of 120 min.

TABLE 12

| | Collection day of cuttings of potato seedlings | | | | | | | | |
|---|---|---|---|---|---|---|---|---|---|
| | 10 | 13 | 16 | 19 | 22 | 25 | 28 | 31 | 34 |
| The amount of collected cuttings/ 5 cm in plant length | 0 | 42 | 126 | 408 | 34 | 311 | 65 | 312 | 77 |

As shown in Table 12, the shoots (sprouts) having a size of 5 cm, generated from the terminal and lateral buds of the in vitro-cultured plantlets planted through stem cutting in DSCAC, could be collected 13 days after planting stem cuttings. Also, the sprouts generated from stem cuttings could be collected every six days in a large amount.

TEST EXAMPLE 13

This test was performed in order to evaluate the seedling quality according to planting through stem cutting of potato seedlings (5 cm to 6 cm in plant length) for replanting, which were collected from DSCAC.

Each test group was cultivated under the following conditions. For perlite culture, a volume of sterile perlite particles 3 cm to 5 cm in diameter was charged to a height of 7 cm into a rectangular plastic basket 47 cm wide×37 cm long×9 cm high. Stem cuttings were planted at intervals of 2 cm while the lower two nodes were buried in the perlite. Nutrient solution was sufficiently supplied every two days in such a way that it flowed on the bottom. For DSCAC, nutrient solution was supplied for 30 min, and the supply of the nutrient solution was interrupted for 120 min. For SSCAC and the cultivation of potato seedlings planted in hydroponic facilities, nutrient solution was supplied for 30 sec, and the supply of the nutrient solution was interrupted for 4 min. During perlite culture, DSCAC and SSCAC, the indoor temperature was maintained at 21° C., and a light level of 7,000 Lux was maintained. The cultivation of potato seedlings in hydroponic facilities was performed under greenhouse conditions of the external environment.

TABLE 13

| | Planting through stem cutting in perlite culture | Planting through stem cutting in DSCAC | Planting through stem cutting in SSCAC | Direct planting in hydroponic facilities |
|---|---|---|---|---|
| Acclimatization of developed roots (%) | 100 | 100 | 100 | 100 |
| Damage due to wilting (%) | 0 | 0 | 0 | 0 |
| Damage due to soft rot (%) | 0 | 0 | 0 | 0 |

As shown in Table 13, potato seedlings for replanting through stem cutting, which were collected from DSCAC, had good quality, and thus had high survival rates even when planted through stem cutting using any culture method or when directly planted.

TEST EXAMPLE 14

This test was performed in order to determine whether the potato seedlings for replanting through stem cutting according to the present invention are useful as potato seedlings for general field cultivation. Using in vitro-grown artificial seed potatoes (1-3 g) as a control, potato seedlings, which were rooted and hardened in the perlite culture of Table 13 for 10 days and acclimatized for 5 days in a greenhouse, plug potato seedlings, which were obtained by planting through stem cutting potato seedlings for replanting through stem cutting in the DSCAC of Table 13 in bed soil in a plug tray, and hardening the planted seedlings in a greenhouse for 15 days, and plug potato seedlings, which were produced by transplanting potato seedlings hardened in perlite culture for 10 days in bed soil in a plug tray, and growing the planted seedlings in a greenhouse for 10 days were planted at intervals of 20 cm in two rows in PE mulching (total 1,200 seedlings/March 21), wherein 2,000 kg of fully fermented compost, 10 kg of nitrogen, 10 kg of phosphoric acid, 12 kg of potassium sulfate and 6 kg of insecticides (Mocap) against soil organisms were tilled into a 300 pyong (one pyong=3.3 m2) field. Seedlings were arranged in a randomized complete block design with three replications. In order to prevent damage due to disease and harmful insects, 160 L of Form-D, 160 L of Mancozeb and 2 kg of Cornido were individually applied two times to the 300 pyong field. Potato harvest and evaluation were performed on June 25.

TABLE 14

|  | Direct | | | Plug seedlings from plug tray | |
| --- | --- | --- | --- | --- | --- |
|  | sowing of artificial seed potatoes | Seedlings produced in DSCAC | Seedlings produced in perlite culute | Seedlings planted in bed soil through stem cutting | Seedlings through transplanting |
| Miss-planted rates upon field planting | 75% | 37% | 21% | 8% | 3% |
| Plant length | 40.2 cm | 46.7 cm | 63.0 cm | 72.0 cm | 89.1 cm |
| Stolon number | 4.8 | 11.4 | 10.1 | 11.5 | 11.4 |
| Shoot tip length | 0.6 cm | 0.7 cm | 0.7 cm | 0.8 cm | 0.8 cm |
| Tuber number/plant | 8.3 | 9.8 | 9.2 | 11.7 | 11.9 |
| Tuber weight/plant | 191 g | 278 g | 311 g | 339 g | 372 g |

As shown in Table 14, the potato seedlings for replanting through stem cutting, which were produced in DSCAC, had good quality, and thus good survival against the stresses of the external environment. Thus, when potato seedlings for direct cultivation in field are required, plug potato seedlings produced using the plug tray are of good quality.

TEST EXAMPLE 15

This test was performed in order to investigate the effects of the leaves, remaining on the ground stems, on rooting when potato seedlings produced in DSCAC were replanted through stem cutting in SSCAC. The replanted seedlings were grown in a nutrient solution, which was supplied for 30 min and interrupted for intervals of 120 min, at room temperature, that is, 21° C., under 7,000 Lux lighting for 18-20 hrs, and 0 Lux for 4-6 hrs. Light radiation was performed two times per day at 9:00 am and 9:0 pm.

TABLE 15

|  | Upper two leaves | Upper four leaves | Upper six leaves | Upper eight leaves |
| --- | --- | --- | --- | --- |
| Rooting day after replanting | 4.5 | 4.5 | 4.5 | 4.0 |
| Damage due to wilting (%) | 0 | 0 | 0 | 0 |
| Damage due to soft rot (%) | 0 | 0 | 0 | 0 |

As shown in Table 15, the leaves remaining on the stems of potato seedlings seldom affected rooting. However, it is preferable to perform stem descending work after all of the leaves except for upper two or three leaves are removed in order to produce seedlings having long stems with many nodes, which are required in hydroponics.

TEST EXAMPLE 16

This test was performed using seedlings grown to 10 cm in order to investigate the effects of the length of roots removed from seedlings on rooting upon stem descending of potato seedlings in SSCAC. The seedlings were grown at an indoor temperature of 21° C. under 7,000 Lux lighting for 18-20 hrs, and 0 Lux for 4-6 hrs. A nutrient solution sprayed onto potato seedlings was supplied for 30 sec, and the supply of the nutrient solution was interrupted for 4 min. The supply and interruption of the nutrient solution were alternately repeated. The roots were considered to be regenerated when they had five or more root hairs and were 0.5 cm or longer.

TABLE 16

|  | The degree of root cut of potato seedlings | | | |
| --- | --- | --- | --- | --- |
|  | No cut | ½ cut | ¾ cut | Complete removal |
| Wilting day of leaves and stems upon planting | 6 | 4 | 3 | 6 |
| Root regeneration day | 6.0 | 4.0 | 4.0 | 4.5 |
| Plant length after 10 days | 12.9 | 15.1 | 16.8 | 14.5 |

As shown in Table 16, the best results were obtained when three quarters of the roots of potato seedlings to be replanted through stem cutting were cut, and the potato seedlings having only one quarter of the roots were subjected to stem descending work.

TEST EXAMPLE 17

This test was performed in order to compare the quality of potato seedlings produced according to the methods described in Table 17. 2,000 potato seedlings were planted and cultivated in hydroponics having an apparatus and a control method for maintaining the environment of root zone at optimal levels.

TABLE 17

|  | Tissue-cultured seedlings/7 cm | Tank-cultured seedlings/8 cm | Seedling sprouts/7 cm | DSCAC seedlings/8 cm | SSCAC seedlings/35 cm |
| --- | --- | --- | --- | --- | --- |
| Days until rooting begins | 6 | 6 | 3 | 4 | 3 |

TABLE 17-continued

|  | Tissue-cultured seedlings/7 cm | Tank-cultured seedlings/8 cm | Seedling sprouts/7 cm | DSCAC seedlings/8 cm | SSCAC seedlings/ 35 cm |
|---|---|---|---|---|---|
| Damaged seedlings upon planting in hydroponics | 63% | 49% | 0% | 16% | 0% |
| Primary stolon number | 8 | 8 | 7 | 11 | 14 |
| Days until reproductive growth phase | 42 | 38 | 33 | 39 | 37 |
| Number of plants over 5 g | 24 | 29 | 27 | 33 | 41 |

As shown in Table 17, potato seedlings produced in DSCAC and SSCAC were found to have the best quality.

TEST EXAMPLE 18

This test was performed in order to establish a method for producing potato seedlings suitable for planting and capable of undergoing rapid rooting when planted in hydroponic facilities. After all of the leaves except for the uppermost three leaves had been removed from potato seedlings grown 30 cm or longer that had undergone the SSCA step of Example 1, the potato seedlings were planted in facilities in which the root zone environment was automatically controlled with respect to the day length and temperature.

TABLE 18

| | States of root zone of potato seedlings planted in hydroponics | | | | |
|---|---|---|---|---|---|
| | ¾ cut seedling on planting day | Seedlings acclimatized for 3 days after ¾ cutting | Seedlings acclimatized for 5 days after ¾ cutting | Seedlings acclimatized for 7 days after ¾ cutting | Seedlings acclimatized for 9 days after ¾ cutting |
| Wilting day of leaves and stems upon planting | 3 | 2 | 0 | 1 | 5 |
| After 10 days Plant length | 16.8 cm | 17.1 cm | 18.3 cm | 17.9 cm | 15.2 cm |
| Root length | 0.6 cm | 0.9 cm | 7.7 cm | 8.4 cm | 0.5 cm |

As shown in Table 18, when seedlings produced in SSCAC were acclimatized for 5 days to 7 days after all of the leaves except for the uppermost three leaves had been removed prior to planting in hydroponic facilities, they underwent better initial growth, leading to high rooting rates.

INDUSTRIAL APPLICABILITY

As described hereinbefore, according to the present invention, when in vitro-cultured plantlets are planted in DSCAC through stem cutting, and sprouts from the terminal and lateral buds of the plantlets are hardened by gradually increasing light levels from the dark condition, the plantlets have healthy dark-green leaves and a high accumulation of carbohydrates, thereby giving rise to potato seedlings having long stems and stems which appear robust and are not overgrown, and elastic and short nodes. When planted in hydroponic facilities, such potato seedlings have high adaptability to the external environment and thus rapidly uniformly generate roots in a short time. The rapid root anchoring prevents planted seedlings from withering, leading to death, growing poorly, and the like.

The direct planting of in vitro plantlets through stem cutting without a separate acclimatization process shortens the overall time required to produce potato seedlings by omitting the acclimatization process.

The DSCA according to the present invention comprises supplying a nutrient solution and interrupting the supply of the nutrient solution. While the supply of the nutrient solution is interrupted, the nutrient solution and growth debris are completely discharged, and the circulating nutrient solution is filtered through a sieving net and then supplied again, thereby preventing soft rot and rot diseases in the roots in the root zone and stems.

In addition, disease-free potato seedlings can be repeatedly collected in the DSCA, making it possible to mass produce disease-free potato seedlings. Thus, the present invention is more cost-effective and less labor-intensive.

Further, the present invention enables the production of robust potato seedlings having many round nodes capable of maximizing the number of stolon and achieving a plant length of 30-40 cm by further subjecting the potato seedlings, having undergone the deep-flow-stem-cutting-and-acclimatization process, to the SSCA step.

What is claimed is:

1. A method of mass producing potato seedlings, comprising:
   collecting growing points of seed potatoes and culturing the growing points in a liquid or solid medium;
   introducing in vitro plantlets obtained from the culture of the growing points to a solid culture, wherein the solid culture is comprised of two-steps: primary shoot subculture and secondary propagation subculture; and
   removing the in vitro plantlets from the solid culture and planting a stem cutting of the in vitro plantlets and acclimatizing the planted stem cutting of the in vitro plantlets in deep flow culture, in which a nutrient solution is circulating, wherein in the acclimatizing, light intensity is gradually increased according to growth phases to gradually harden the planted stem cutting of the in vitro plantlets, wherein the light intensity is gradually increased from:
a) 0 Lux for 55-65 hours, followed by
b) 2,100 Lux for 45-55 hours, followed by 0 Lux for 4-8 hours, followed by
c) 3,600 Lux for 35-45 hours, followed by 0 Lux for 4-8 hours, followed by
d) 5,500 Lux for 25-35 hours, followed by 0 Lux for 4-8 hours, followed by
e) 7,000 Lux for 535-545 hours, followed by 0 Lux for 120-180 hours.

2. The method according to claim 1, wherein the growing points of seed potatoes are cultured for a period ranging from 24 to 26 days at 18-22° C. under 900-1,100 Lux lighting for 18-20hrs, and 0 Lux for 4-6 hrs in a basic MS medium of pH 5.7-5.8 supplemented with 28-32 g/L of sucrose, or in the medium further supplemented with 7-11 g/L of agar.

3. The method according to claim 1, further comprising performing pathogen testing for the in vitro plantlets after the growing points of seed potatoes are cultured.

4. The method according to claim 1, wherein the primary shoot subculture is carried out in a basic MS medium of pH 5.7-5.8, which is supplemented with 7-11 g/L of agar and 70-80 g/L of sucrose.

5. The method according to claim 1, wherein the secondary propagation culture is carried out in a basic MS medium of pH 5.7-5.8, which is supplemented with 7-11 g/L of agar, 70-80 g/L of sucrose, and 0.020-0.035 mg/L of coumarin.

6. The method according to claim 1, wherein the primary shoot subculture and the secondary propagation culture are individually carried out for 25-35 days at 18-22° C. under 4,000-5,000 Lux lighting for 18-20 hrs, and 0 Lux for 4-6 hrs.

7. The method according to claim 1, wherein the planted cuttings of the in vitro plantlets have stems from which all leaves have fallen.

8. The method according to claim 1, wherein the planted cuttings of the in vitro plantlets are cut at node regions at a lower part of stems with a disinfected sharp knife.

* * * * *